(12) United States Patent
Delisa et al.

(10) Patent No.: US 9,879,252 B2
(45) Date of Patent: Jan. 30, 2018

(54) PROTEIN DISCOVERY USING INTRACELLULAR RIBOSOME DISPLAY

(75) Inventors: Matthew P. Delisa, Ithaca, NY (US);
Lydia Contreras-Martinez, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 52 days.

(21) Appl. No.: 12/671,446

(22) PCT Filed: Jul. 31, 2008

(86) PCT No.: PCT/US2008/071747
§ 371 (c)(1),
(2), (4) Date: Jul. 19, 2010

(87) PCT Pub. No.: WO2009/018438
PCT Pub. Date: Feb. 5, 2009

(65) Prior Publication Data
US 2011/0008774 A1    Jan. 13, 2011

Related U.S. Application Data

(60) Provisional application No. 60/953,050, filed on Jul. 31, 2007.

(51) Int. Cl.
*C12Q 1/68* (2006.01)
*C12N 15/10* (2006.01)

(52) U.S. Cl.
CPC .............................. *C12N 15/1041* (2013.01)

(58) Field of Classification Search
CPC .................... C12N 15/1041; C12N 15/1034
See application file for complete search history.

(56) References Cited

U.S. PATENT DOCUMENTS

| 5,922,545 A * | 7/1999 | Mattheakis et al. .............. 506/9 |
| 6,194,550 B1 * | 2/2001 | Gold et al. ..................... 530/358 |
| 2003/0165945 A1 | 9/2003 | Bird et al. |
| 2004/0265984 A1 | 12/2004 | Yonath et al. |
| 2006/0177862 A1 | 8/2006 | Osbourn et al. |

OTHER PUBLICATIONS

Schraml et al., "In vitro protein engineering approaches for the development of biochemical, diagnistic and therapeutic tools" Dissertation, Nov. 16, 2005, catalogue No. urn:nbn:de:gbv:3-000009684.*

(Continued)

*Primary Examiner* — Reza Ghafoorian
(74) *Attorney, Agent, or Firm* — LeClairRyan, a Professional Corporation

(57) ABSTRACT

The present invention relates to a method of identifying a protein that binds to a target molecule and has intracellular functionality. This method includes providing a construct comprising a deoxyribonucleic acid molecule encoding the protein which binds to the target molecule, with the deoxyribonucleic acid molecule being coupled to a stall sequence. A host cell is transformed with the construct and then cultured under conditions effective to form, within the host cell, a complex of the protein whose translation has been stalled, the mRNA encoding the protein, and ribosomes. The protein in the complex is in a properly folded, active form and the complex is recovered from the cell.

34 Claims, 7 Drawing Sheets

(56) References Cited

OTHER PUBLICATIONS

Evans et al. "Homogeneous stalled ribosome nascent chain complexes produced in vivo or in vitro", Nature Methods, vol. 2 No. 10, Oct. 2005.*

Hanes et al., "In vitro selection and evolution of functional proteins by using ribosome display," Proc. Natl. Acad. Sci. USA vol. 94, pp. 4937-4942, May 1997.*

Sunohara et al. Ribosome Stalling during Translation Elongation Induces Cleavage of mRNA Being Translated in *Escherichia coli*, The Journal of Biological Chemistry, vol. 279, No. 15, Issue of Apr. 9, pp. 15368-15375, 2004.*

Fitzgerald et al., Protein complex expression by using multigene baculoviral vectors, Nature Methods, vol. 3 No. 12, Dec. 2006, 1021-1032.*

Evans et al., "Homogeneous Stalled Ribosome Nascent Chain Complexes Produced in Vivo or in Vitro," and Supplementary Methods, Nat. Methods 2(10):757-62 (2005).

PCT International Search Report and Written Opinion for PCT/US2008/071747 dated Dec. 12, 2009.

International Preliminary Report on Patentability for corresponding PCT/US2008/071747 (dated Feb. 2, 2010).

\* cited by examiner

PROTEIN DISCOVERY USING INTRACELLULAR RIBOSOME DISPLAY

This application claims the benefit of U.S. Provisional Patent Application Ser. No. 60/953,050, filed Jul. 31, 2007, which is hereby incorporated by reference in its entirety.

This invention was made with government support under grant number CBET 0449080 (OSP #47241) awarded by National Science Foundation. The government has certain rights in this invention.

FIELD OF THE INVENTION

The present invention relates to protein discovery using intracellular ribosome display.

BACKGROUND OF THE INVENTION

Ribosome display is a powerful approach for affinity and stability maturation of recombinant antibodies. However, since ribosome display is performed entirely in vitro, there are several limitations to this approach including technical challenges associated with: (i) efficiently expressing and stalling antibodies on ribosomes using cell-free translation mixtures; and (ii) folding of antibodies in buffers where the concentration and composition of factors varies from that found in the intracellular milieu.

Since the development of hybridoma technology in 1975 (Kohler et al., "Continuous Cultures of Fused Cells Secreting Antibody of Predefined Specificity," *Nature* 256:495-7 (1975)) and, more recently, the development of various in vitro antibody display technologies, (Amstutz et al., "In vitro Display Technologies: Novel Developments and Applications," *Curr Opin Biotechnol* 12:400-5 (2001); Dower et al., "In vitro Selection as a Powerful Tool for the Applied Evolution of Proteins and Peptides," *Curr Opin Chem Biol* 6:390-8 (2002); Lipovsek et al., "In vitro *Protein Evolution by Ribosome Display and mRNA Display*," *J Immunol Methods* 290:51-67 (2004); Rothe et al., "In vitro Display Technologies Reveal Novel Biopharmaceutics," *FASEB J* 20, 1599-610 (2006); and Wark et al., "Latest Technologies for the Enhancement of Antibody Affinity," *Adv Drug Deliv Rev* 58:657-70 (2006)) 18 FDA-approved therapeutic antibody products are currently on the market. With many more antibodies in various stages of clinical development, their importance is expected to escalate in the coming years (Holliger et al., "Engineered Antibody Fragments and the Rise of Single Domains," *Nat Biotechnol* 23:1126-36 (2005); Hoogenboom, H. R., "Selecting and Screening Recombinant Antibody Libraries," *Nat Biotechnol* 23:1105-16 (2005); Reichert et al., "Monoclonal Antibody Successes in the Clinic," *Nat Biotechnol* 23:1073-8 (2005); and Hudson et al., "Engineered Antibodies," *Nat Med* 9:129-34 (2003)). Recently, innovative recombinant DNA techniques, such as chimerization and humanization, have opened the door to molecular reformatting of naturally produced full-length antibodies into smaller synthetic fragments. These formats exhibit many superior biophysical and biochemical properties and can typically be produced more efficiently and economically (Holliger et al., "Engineered Antibody Fragments and the Rise of Single Domains," *Nat Biotechnol* 23:1126-36 (2005)). One such format, the single-chain variable fragment (scFv), consists of covalently linked variable domains ($V_H$ and $V_L$) that retain antigen-binding specificity and offers a more suitable format for expression and protein engineering in bacteria and yeast.

The scFv also shows great promise for binding and inactivating target antigens in an intracellular compartment such as the cytoplasm (Biocca et al., "Expression and Targeting of Intracellular Antibodies in Mammalian Cells," *EMBO J* 9:101-8 (1990) and Biocca et al., "Intracellular Immunization with Cytosolic Recombinant Antibodies," *Biotechnology (N Y)* 1:396-9 (1994)). In principle, the binding properties exhibited by monoclonal antibodies in the extracellular environment should be transferable to the inside of a living cell using intracellularly expressed scFvs, commonly referred to as intrabodies. However, despite the promise of intrabodies, cytoplasmic expression of scFvs is generally confronted with difficulties concerning stability, solubility, and aggregation. The primary reason for these difficulties is that the two conserved intradomain disulfide bonds found in scFvs cannot form under the reducing conditions of the cytoplasm. As disulfide bridges are known to contribute ~5 kcal/mol to the overall stability of an scFv (Frisch et al., "Contribution of the Intramolecular Disulfide Bridge to the Folding Stability of REIv, the Variable Domain of a Human Immunoglobulin Kappa Light Chain," *Fold Des* 1:431-40 (1996)), lack of disulfide bonds typically results in scFv destabilization (Proba et al., "A Natural Antibody Missing a Cysteine in VH: Consequences for Thermodynamic Stability and Folding," *J Mol Biol* 265:161-72 (1997)), decreased intracellular solubility (Martineau et al., "Expression of an Antibody Fragment at High Levels in the Bacterial Cytoplasm," *J Mol Biol* 280:117-27 (1998)), limited half-life (Cattaneo et al., "The Selection of Intracellular Antibodies," *Trends Biotechnol* 17:115-21 (1999)), and loss of activity (Martineau et al., "Expression of an Antibody Fragment at High Levels in the Bacterial Cytoplasm," *J Mol Biol* 280:117-27 (1998)). Furthermore, the most commonly used approaches for selecting antibodies in the laboratory, including, for example, cell surface display and phage display, yield scFvs that are typically non-functional in the reducing cytoplasm (Visintin et al, "Selection of Antibodies for Intracellular Function Using a Two-Hybrid in vivo System," *Proc Natl Aced Sci USA* 96:11723-8 (1999)) likely due to the fact that the expression and isolation process occurs under non-reducing conditions.

Plückthun and coworkers elegantly demonstrated that in vitro ribosome display (Hanes et al., "In vitro Selection and Evolution of Functional Proteins by Using Ribosome Display," *Proc Natl Acad Sci USA* 94:4937-42 (1997) and Mattheakis et al., "An in vitro Polysome Display System for Identifying Ligands from Very Large Peptide Libraries," *Proc Natl Acad Sci USA* 91:9022-6 (1994)), whereby stabilized antibody, ribosome, and mRNA (ARM) complexes are generated entirely in vitro, can be used for isolating scFvs that are stable under reducing conditions. This was achieved simply by altering the redox potential of the buffer in which the folding of the displayed protein occurred (Jermutus et al., "Tailoring in vitro Evolution for Protein Affinity or Stability," *Proc Natl Acad Sci USA* 98:75-80 (2001)). However, this strategy required five rounds of mutagenesis and selection. Furthermore, numerous successes notwithstanding (Lipovsek et al., "In vitro Protein Evolution by Ribosome Display and mRNA Display," *J Immunol Methods* 290:51-67 (2004)), in vitro ribosome display can be limited in usefulness, because: (i) efficient in vitro translation and stalling can be technically challenging; (ii) concentrations of cellular factors that may be required for efficient scFv folding differ from concentrations found in vivo; and (iii) in vivo verification is ultimately needed to ensure that any functional improvements discovered in vitro are reproducible inside host cells, where the scFv will be expressed for either in vivo applications or for manufacturing.

The present invention is directed to overcoming these and other deficiencies in the art.

SUMMARY OF THE INVENTION

One aspect of the present invention relates to a method of identifying a protein that binds to a target molecule and has intracellular functionality. This method includes providing a construct comprising a deoxyribonucleic acid molecule encoding the protein which binds to the target molecule, with the deoxyribonucleic acid molecule being coupled to a stall sequence. A host cell is transformed with the construct and then cultured under conditions effective to form, within the host cell, a complex of the protein whose translation has been stalled, the mRNA encoding the protein, and ribosomes. The protein in the complex is in a properly folded, active form and the complex is recovered from the cell.

Another aspect of the present invention relates to a construct which includes a deoxyribonucleic acid molecule encoding a protein that binds to a target molecule and an SecM stalling sequence coupled to the deoxyribonucleic acid molecule. The deoxyribonucleic acid molecule and the SecM stalling sequence are coupled with sufficient distance between them to permit expression of their encoded protein, within the cell, in a properly folded, active form.

Another aspect of the present invention relates to a method of identifying a protein that binds to a target molecule and has intracellular functionality. This method includes providing a construct comprising a deoxyribonucleic acid molecule encoding the protein which binds to the target molecule, said deoxyribonucleic acid molecule being coupled to a stall sequence. A cell-free extract preparation containing ribosomes is also provided. The method further involves contacting the construct with the cell-free extract preparation containing ribosomes under conditions effective for ribosome translation and the formation of a complex of the protein whose translation has been stalled, the mRNA encoding the protein, and the ribosomes. The protein in the complex is in a properly folded, active form and the complex is recovered.

Applicants have developed a novel method for intracellular ribosome display that takes advantage of the recently discovered *Escherichia coli* SecM translation arrest mechanism. This is the first evidence that the encoding mRNA of SecM-stalled heterologous proteins remains stably attached to ribosomes, thereby enabling creation of stalled antibody-ribosome-mRNA (ARM) complexes entirely inside of living cells. Since ARM complexes faithfully maintain a genotype-phenotype link between the arrested antibody and its encoding mRNA, this method is ideally suited for isolating stability-enhanced single-chain variable fragment (scFv) antibodies that are efficiently folded and functional in the bacterial cytoplasm.

To eliminate these shortcomings, a novel ribosome display approach that employs the recently discovered *Escherichia coli* SecM translation arrest mechanism (Nakatogawa et al., "The Ribosomal Exit Tunnel Functions as a Discriminating Gate," *Cell* 108, 629-36 (2002), which is hereby incorporated by reference in its entirety) has been developed. This development was facilitated by applicants finding that the encoding mRNA of SecM-stalled heterologous proteins remained stably attached to ribosomes; hence, intact ARM complexes could be created for the first time on the inside of living cells (See FIG. 1A). Since stalled complexes maintain a genotype-phenotype link between a displayed scFv and its encoding mRNA, SecM-mediated ribosome display is ideally suited for engineering recombinant antibodies. Moreover, since scFv synthesis and stalling on ribosomes is performed in the cytoplasm of intact cells, intracellular ribosome display naturally selects for proteins that are correctly folded and soluble under reducing conditions, in the face of macromolecular crowding and in the presence of all cellular factors (e.g., chaperones, isomerases, proteases, etc.) that impact protein solubility. In support of this notion, cytoplasmic stability, and thus intracellular function, of an scFv can be enhanced 2-3 fold after only a single round of mutagenesis and selection using intracellular ribosome display. The novelty of this approach lies in the fact that intact, highly stable ARM complexes can be created inside cells and that these complexes can be isolated selectively for stability engineering of antibodies in the cytoplasm. By capitalizing on the recently discovered SecM translation arrest mechanism in this manner, ribosome display for in vivo applications such as the development of intrabodies can be achieved.

BRIEF DESCRIPTION OF THE DRAWINGS

As shown in FIG. 1A, a plasmid-encoded scFv library is first amplified by PCR, whereby a flexible linker sequence and SecM17 fusion partner are introduced. Next, after transformation of the plasmid library into *E. coli*, expression of scFv-SecM17 fusions is induced; mRNA is transcribed and translated entirely in vivo. If different factors are needed for enhancing the folding of the scFvs on the ribosomes (e.g., chaperones), these can be provided via a plasmid and co-expressed. Following induction, 70S ribosome complexes are isolated from bacteria using sucrose cushion centrifugation. The desired ribosome complexes are affinity selected from the ribosome preparations by binding of the native scFv to the immobilized antigen. Non-specific ribosome complexes are removed by intensive washing and the bound ribosome complexes are dissociated by EDTA (or whole complexes can be specifically eluted with antigen). RNA is isolated from the dissociated ARM complexes and reverse transcribed to cDNA. The resulting cDNA is amplified by PCR, and the PCR product is then used for the next cycle of enrichment, with a portion being analyzed by cloning and sequencing and/or by ELISA. FIG. 1B shows a schematic drawing of unfused and SecM17-fused scFv constructs which include: a FLAG epitope tag (F); the anti-β-gal scFv13 sequence; a c-Myc epitope tag (M); a 6×-his tag (H); a thrombin cleavage site (T); a flexible Gly-Ser linker (GS); a SecM stall sequence, FST-PVWISQAQGIRAGP (SEQ ID NO: 1); and a stop codon (star).

FIG. 2A is a Western blot analysis of soluble fractions isolated from BL21(DE3) *E. coli* cells, expressing unfused (upper panel) or SecM17-fused (lower panel) wt scFv13 (wt) or solubility-enhanced scFv13-R4 (R4) using anti-FLAG IgG. Induced (+) and uninduced (−) samples are shown for scFv13-SecM17 fusions. An equivalent amount of total protein was loaded in each lane. FIG. 2B shows a normalized ELISA signal from soluble fractions prepared from cells expressing the unfused or SecM17-fused scFv constructs as indicated on β-gal-coated plates. An equivalent amount of total protein was assayed in each well. Absorbance values for each sample were normalized to the absorbance measured for the value for scFv13-R4-SecM17. Data is the average of three replicate experiments and error bars represent the standard error of the mean.

FIG. 4C show the results of whole cell β-gal assays of intact X-gal treated AMEF 959 cells expressing wt scFv13 or related variants from plasmid pTrc99A. An equivalent number of cells were analyzed in each well. AMEF β-gal activation is reported as the change in X-gal hydrolysis for 959 cells expressing an scFv13 variant normalized to the change in X-gal hydrolysis for 959 cells expressing scFv13-R4. Data is the average of six replicate experiments and the error bars represent the standard error of the mean. Absorbance values for each sample were normalized to the absorbance measured for scFv13-R4-expressing cells.

FIG. 5A shows the amino acid sequence alignment of wt scFv13 (SEQ ID NO: 2) and related variants, S20 (SEQ ID NO: 3) and S23 (SEQ ID NO: 4). The sequence of wt scFv13 is written in single letter amino acid code. Numbering of amino acid residues in $V_H$ and $V_L$, and the labeling of CDRs is according to Kabat numbering scheme. Immunodetection epitopes are italicized. FIG. 5B shows the location of mutations for clones S20 and S23 in scFv13 structure. The structure was previously modeled by homology (Martineau, et. al., "Expression of an Antibody Fragment at High Levels in the Bacterial Cytoplasm," *J. Mol. Biol.* 280: 117-27 (1998), which is hereby incorporated by reference in its entirety). The drawing was generated with MacPyMOL. The $V_H$ is shown in olive, the $V_L$ in green, the disulfide bonds in black, and the mutations for clones S20 and S23 in red and purple, respectively. Asterisks indicate mutations that are shared between selected variants and those isolated previously by Martineau, et. al., "Expression of an Antibody Fragment at High Levels in the Bacterial Cytoplasm," *J. Mol. Biol.* 280: 117-27 (1998), which is hereby incorporated by reference in its entirety).

DETAILED DESCRIPTION OF THE INVENTION

Figure 1:
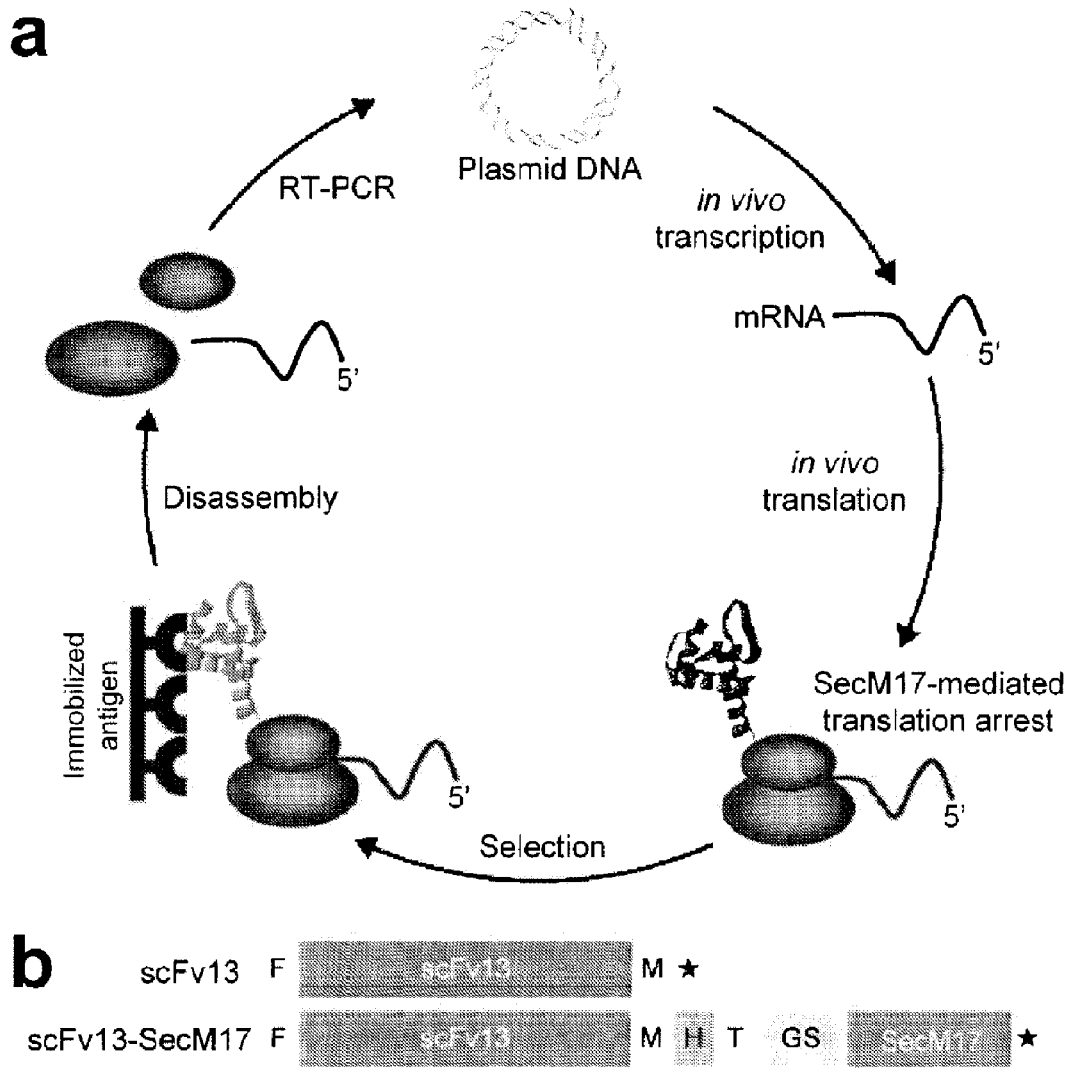
FIG. 1A-B illustrate the principle of intracellular ribosome display for affinity and stability maturation of protein (scFv) libraries in accordance with the present invention.

One aspect of the present invention relates to a method of identifying a protein that binds to a target molecule and has intracellular functionality. This method includes providing a construct comprising a deoxyribonucleic acid molecule encoding the protein which binds to the target molecule, with the deoxyribonucleic acid molecule being coupled to a stall sequence. A host cell is transformed with the construct and then cultured under conditions effective to form, within the host cell, a complex of the protein whose translation has been stalled, the mRNA encoding the protein, and ribosomes. The protein in the complex is in a properly folded, active form and the complex is recovered from the cell.

The protein that binds to the target molecule having intracellular functionality of the present invention can include any ligand binding protein. Suitable ligand binding proteins, include high-affinity antibody fragments (e.g., Fab, Fab' and F(ab')$_2$), single-chain Fv antibody fragments, nanobodies or nanobody fragments, fluorobodies, or aptamers. In a preferred embodiment of the present invention, the protein is a single-chain variable fragment antibody, an antibody in which the heavy chain and the light chain of a traditional two chain antibody have been joined to form one chain. Typically, a linker peptide is inserted between the two chains to allow for proper folding and creation of an active binding site. The methods of the present invention can be used to generate libraries of single-chain antibodies that are cytoplasmically stable and intracellularly functional. The libraries of single-chain antibodies are useful for screening and selection of antibodies having the desired high-affinity binding properties.

Other ligand binding proteins suitable for use in the methods of the present invention include biotin-binding proteins, lipid-binding proteins, periplasmic binding proteins, lectins, serum albumins, enzymes, phosphate and sulfate binding proteins, immunophilins, metallothionein, or various other receptor proteins. The method of the present invention can be used to generate peptide libraries that are useful for screening high-affinity ligand binding partners.

In accordance with the method of the present invention, a deoxyribonucleic acid molecule encoding the protein of interest is coupled to a stall sequence. A stall sequence, as used herein, is any sequence that interacts with residues in the ribosomal exit tunnel to stall translation, resulting in the display of the protein of interest on the ribosome surface. In a preferred embodiment of the present invention, the stall sequence is derived from the *E. coli* SecM protein (synonym="ECK0098, JW5007, yacA, srrA") and has the amino acid sequence of SEQ ID NO:1: FSTPVWISQAQ-GIRAGP. The SecM stall sequence is encoded by a nucleic acid sequence set forth in SEQ ID NO: 28: ttc agc acg ccc gtc tgg ata agc cag gcg caa ggc atc cgt get ggc cct. This corresponds to DNA bases 448-498 of the secM gene. See Schmidt, et al., "Nucleotide Sequence of the secA Gene and secA (Ts) Mutations Preventing Protein Export in *Escherichia Coli*," *J. Bacteriol.* 170:3404-14 (1988), which is hereby incorporated by reference in its entirety. A consensus for the SecM protein is FXXXXWIXXXXGIRAGP; where X can be any amino acid (SEQ ID NO: 26).

Other suitable stall sequences includes: (1) cat leader 5-mer peptide from Gram-positive bacteria; and (2) cmlA leader 8-mer peptide from Gram-negative bacteria (see Lovett, et al., "Nascent Peptide Regulation of Translation," *J Bacteriol* 176(21):6415-7 (1994), which is hereby incorporated by reference in its entirety).

Generating proteins of interest according to the methods of the present invention can be carried out using the techniques described herein or using any other standard technique known in the art. For example, the fusion protein, i.e. the protein of interested coupled to a stall sequence, can be prepared by translation of an in-frame fusion of the deoxyribonucleic acid molecule encoding the protein of interest and the polynucleotide stall sequences, i.e., a hybrid gene. The hybrid gene encoding the fusion polypeptide is inserted into an expression vector which is used to transform or transfect a host cell. Alternatively, the deoxyribonucleic acid molecule encoding the protein or polypeptide of interest is inserted into an expression vector in which the polynucleotide encoding the stall polypeptide is already present. The stall polypeptide or protein of the fusion protein is preferably fused to the C-terminal, end of the protein or polypeptide of interest.

Fusions between the deoxyribonucleic acid molecule encoding the protein or polypeptide of interest and a stall polynucleotide sequence may be such that the nucleic acid sequence encoding the protein or polypeptide of interest is directly contiguous with the nucleic acid sequence encoding the stall polypeptide or protein of the present invention. Alternatively, the deoxyribonucleic acid molecule encoding the protein of interest may be coupled to the stall polynucleotide sequence by way of a linker sequence such as the flexible 8-residue Gly-Ser linker described herein having the sequence, AGSAAGSG (SEQ ID NO:27). The Gly-Ser linker may comprise between 10-50 Gly/Ser units depending on the optimal separation needed between the ribosome and the target protein. In addition to a Gly-Ser linker, other suitable linkers include a Gly linker or the flexible linkers from an immunoglobulin disclosed in U.S. Pat. No. 5,516,637 to Huang et al, which is hereby incorporated by reference in its entirety. The linker may also contain a protease-specific cleavage site so that the protein of interest may be controllably released from the stall polypeptide or protein. Examples of protease sites include those specific to cleavage by factor Xa, enterokinase, collagenase, Igase (from *Neisseria gonorrhoeae*), thrombin, and TEV (Tobacco Etch Virus) protease.

In addition to a flexible linker and a protease-specific cleavage site, one or more polynucleotide encoding marker proteins can also be positioned between the deoxyribonucleic acid molecule encoding the protein of interest and the stall polynucleotide sequence. Marker proteins are well known in the art and include affinity protein markers, such as chitin binding protein, maltose binding protein, glutathione-s-transferase, and the poly(His) tag; epitope markers, such as the V5-tag, c-myc-tag, HA-tag, or FLAG-tag. In a preferred embodiment of the present invention, a c-Myc epitope tag, a 6×-His tag, a thrombin cleavage site, and a linker are all positioned within the construct between the deoxyribonucleic acid molecule encoding the protein of interest and stalling sequence.

The nucleic acid construct containing the deoxyribonucleic acid molecule encoding the protein of interest and the stall polynucleotide with the optional c-Myc epitope tag, 6×-His tag, thrombin cleavage site, and linker positioned in between, preferably also contains a polynucleotide sequence encoding a marker sequence upstream (5') of the deoxyribonucleic acid molecule encoding the protein of interest. Any of the marker proteins mentioned above (i.e. chitin binding protein, maltose binding protein, glutathione-s-transferase, and the poly(His) tag; epitope markers, such as the V5-tag, c-myc-tag or the HA-tag) are suitable. In a preferred embodiment, a polynucleotide encoding a FLAG-tag is inserted upstream of the deoxyribonucleic acid molecule encoding the protein of interest. Finally, a stop codon is inserted at the 3' end of the polynucleotide encoding the stall sequence.

Once the fusion protein is constructed, the nucleic acid construct encoding the fusion protein is inserted into an expression system to which the molecule is heterologous. The heterologous nucleic acid molecule is inserted into the expression system or vector in proper sense (5'→3') orientation relative to the promoter and any other 5' regulatory molecules, and correct reading frame. The preparation of the nucleic acid constructs can be carried out using standard cloning methods well known in the art as described by Sambrook et al., *Molecular Cloning: A Laboratory Manual*, Cold Springs Laboratory Press, Cold Springs Harbor, N.Y. (1989), which is hereby incorporated by reference in its entirety. U.S. Pat. No. 4,237,224 to Cohen and Boyer, which is hereby incorporated by reference in its entirety, also describes the production of expression systems in the form of recombinant plasmids using restriction enzyme cleavage and ligation with DNA ligase.

Suitable expression vectors include those which contain replicon and control sequences that are derived from species compatible with the host cell. For example, if *E. coli* is used as a host cell, plasmids such as pUC19, pUC18 or pBR322 may be used. Other suitable expression vectors are described in *Molecular Cloning: a Laboratory Manual:* 3rd edition, Sambrook and Russell, 2001, Cold Spring Harbor Laboratory Press, which is hereby incorporated by reference in its entirety. Many known techniques and protocols for manipulation of nucleic acid, for example in preparation of nucleic acid constructs, mutagenesis, sequencing, introduction of DNA into cells and gene expression, and analysis of proteins, are described in detail in *Current Protocols in Molecular Biology*, Ausubel et al. eds., (1992), which is hereby incorporated by reference in its entirety.

Different genetic signals and processing events control many levels of gene expression (e.g., DNA transcription and messenger RNA ("mRNA") translation) and subsequently the amount of fusion protein that is displayed on the ribosome surface. Transcription of DNA is dependent upon the presence of a promoter, which is a DNA sequence that directs the binding of RNA polymerase, and thereby promotes mRNA synthesis. Promoters vary in their "strength"

(i.e., their ability to promote transcription). For the purposes of expressing a cloned gene, it is desirable to use strong promoters to obtain a high level of transcription and, hence, expression and surface display. Therefore, depending upon the host system utilized, any one of a number of suitable promoters may also be incorporated into the expression vector carrying the deoxyribonucleic acid molecule encoding the protein of interest coupled to a stall sequence. For instance, when using *E. coli*, its bacteriophages, or plasmids, promoters such as the T7 phage promoter, lac promoter, trp promoter, recA promoter, ribosomal RNA promoter, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene.

Translation of mRNA in prokaryotes depends upon the presence of the proper prokaryotic signals, which differ from those of eukaryotes. Efficient translation of mRNA in prokaryotes requires a ribosome binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts and Lauer, *Methods in Enzymology*, 68:473 (1979), which is hereby incorporated by reference in its entirety.

Host cells suitable for expressing and displaying the fusion protein on the ribosome surface include any one of the more commonly available gram negative bacteria. Suitable microorganisms include *Pseudomonas aeruginosa, Escherichia coil, Salmonella gastroenteritis (typhimirium), S. typhi, S. enteriditis, Shigella flexneri, S. sonnie, S dysenteriae, Neisseria gonorrhoeae, N. meningitides, Haemophilus influenzae H. pleuropneumoniae, Pasteurella haemolytica, P. multilocida, Legionella pneumophila, Treponema pallidum, T. denticola, T. orales, Borrelia burgdorferi, Borrelia* spp. *Leptospira interrogans, Klebsiella pneumoniae, Proteus vulgaris, P. morganii, P. mirabilis, Rickettsia prowazeki, R. typhi, R. richettsii, Porphyromonas (Bacteriodes) gingivalis, Chlamydia psittaci, C. pneumoniae, C. trachomatis, Campylobacter jejuni, C. intermedis, C. fetus, Helicobacter pylori, Francisella tularenisis, Vibrio cholerae, Vibrio parahaemolyticus, Bordetella pertussis, Burkholderie pseudomallei, Brucella abortus, B. susi, B. melitensis, B. canis, Spirillum minus, Pseudomonas mallei, Aeromonas hydrophila, A. salmonicida*, and *Yersinia pestis*.

In a preferred embodiment of the present invention, the host cell is *E. coli*. An additional preferred embodiment includes the utilization of an *E. coli* host strain carrying mutations in the both thioredoxin reductase (trxB) and glutathione reductase (gar) genes (e.g., Origami™) wherein disulfide bond formation in the cytoplasm is significantly enhanced. Use of a trxB gor mutant strain can be used to affinity- and/or stability-mature scFvs that are stalled and folded under oxidizing conditions.

In addition to bacteria cells, eukaryotic cells such as mammalian and yeast, and baculovirus systems are also suitable host cells that can be used in accordance with the methods of the present invention. Mammalian cell lines available in the art for expression of a heterologous polypeptide include Chinese hamster ovary cells, HeLa cells, baby hamster kidney cells, COS cells and many others. Methods for transforming/transfecting host cells with expression vectors are well-known in the art and depend on the host system selected, as described in Sambrook et al., *Molecular Cloning: A Laboratory Manual*, Cold Springs Laboratory Press, Cold Springs Harbor, N.Y. (1989), which is hereby incorporated by reference in its entirety. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation, and transfection using bacteriophage.

Following transformation of the host cell with an expression vector comprising the nucleic acid construct encoding the protein of interest fused to the stall polypeptide, display of the protein of interest on the ribosome surface is achieved via the stall polypeptide.

Within the host cell, a complex of the stabilized protein whose translation has been stalled, the mRNA encoding the protein, and ribosomes form. When the protein of interest is an antibody, this complex is referred to as an "ARM" complex, i.e. antibody-ribosome and mRNA complex. Recovering the complex from the host cell can be carried out by affinity selection with an agent specific for the protein. To recover the complex from the host cell, cellular ribosome fractions are prepared and incubated with an immobilized antigen, protein binding partner, or marker protein binding partner that specifically recognizes and selectively binds to the protein of interest or marker protein that is displayed on the surface of the ribosome. The antigen, protein binding partner, or marker binding protein can be immobilized on any solid surface or support, such as a polystyrene microtiter plate, column, or a magnetic bead (e.g. Dynabeads®) Alternatively, the antigen or protein binding partner can be co-expressed in vivo, in the cell, along with the protein of interest displayed on the ribosome. When recovering the complex based on the marker protein, such as the FLAG-tag, V5-tag, c-myc-tag or the HA-tag, the marker binding protein can be an antibody recognizing the epitope tag immobilized on the solid support. Alternatively, when marker proteins having a polyhistidine-tag (His-tag) are used, the complex can be recovered using affinity purification media such as, NTA-agarose, HisPur resin or Talon resin.

Dissociating the bound protein-mRNA-ribosome complex from the solid support can be carried out using any appropriate chelating or elution buffer readily used in the art. In a preferred embodiment, the protein-mRNA-ribosome complex is dissociated using EDTA.

The method of the present invention additionally includes isolating the mRNA from the recovered complex. The isolated mRNA is reverse transcribed to form a cDNA encoding the protein, and a construct, comprising the cDNA coupled to the stall sequence, is formed. The steps of transforming, culturing, and recovering, as described above, are repeated to enrich the protein recovered.

Methods for isolating and reverse transcribing RNA are well known in the art (See *Laboratory Techniques in Biochemistry and Molecular Biology: Hybridization with Nucleic Acid Probes. Part I. Theory and Nucleic Acid Preparation*, P. Tijssen, ed., (1993), which is hereby incorporated by reference in its entirety) and any such method of RNA preparation that produces enzymatically manipulatable mRNA or analyzable RNA can be used in accordance with the present invention. For example, the RNA can be isolated by using the guanidinium isothiocyanate-ultracentrifugation method, the guanidinium and phenol-chloroform method, the lithium chloride-SDS-urea method or poly A+/mRNA from tissue lysates using oligo(dT) cellulose method. It is important when isolating the RNA that enough high quality RNA is isolated. Once isolated, the mRNA can be reverse transcribed to form cDNA using any commercially available kit following manufacturer's instructions. Typically, the reaction is carried out using either oligo-dT or random decamer primers and a the reverse transcriptase enzyme.

The steps of transforming, culturing, and recovering, as described above, are repeated to enrich the protein recovered. The enriched protein can be characterized by direct amino acid sequencing. Generally, protein sequencing is carried out using mass spectrometry or Edman degradation reaction. The protein can further be characterized based on affinity screening (i.e. is ability to bind to a ligand binding partner) using an panning, chromatography, or an ELISA based assay. The protein can also be characterized by its activity in an enzyme based assay.

The stability of the identified protein of the present invention can be enhanced by altering or optimizing cellular conditions. Stability can generally be defined as the propensity of a molecule to exist in its folded and active state. Since stalled proteins, i.e. proteins that are displayed on the surface of the ribosome due to stalled translation, undergo folding in the cytoplasm, potent molecular chaperones and/or isomerases can be co-expressed in the host cell to enhance the stability, solubility and/or native folding capacity. Preferred molecular chaperones include DnaK, DnaH, GrpE, GroEL, or GroES and a preferred isomerase is the protein disulfide isomerase. The stability of the identified protein can also be enhanced via the addition of oxidized and reduced glutathione. The stability of the identified protein can further be enhanced by mutating the deoxyribonucleic acid molecule encoding the protein to produce variant nucleic acid sequences encoding variants with amino acid sequences. Methods of site directed or random mutagenesis are well known in the art and are suitable for use in the method of the present invention (See *Current Protocols in Molecular Biology*, Ausubel et al. eds., (1992), which is hereby incorporated by reference in its entirety).

Another aspect of the present invention relates to a construct which includes a deoxyribonucleic acid molecule encoding a protein that binds to a target molecule and an SecM stalling sequence coupled to the deoxyribonucleic acid molecule. The deoxyribonucleic acid molecule and the SecM stalling sequence are coupled with sufficient distance between them to permit expression of their encoded protein, within the cell, in a properly folded, active form.

This construct can be incorporated into an expression vector or a host cell as described above.

Another aspect of the present invention relates to a method of identifying a protein that binds to a target molecule and has intracellular functionality. This method includes providing a construct comprising a deoxyribonucleic acid molecule encoding the protein which binds to the target molecule, said deoxyribonucleic acid molecule being coupled to a stall sequence. A cell-free extract preparation containing ribosomes is also provided. The method further involves contacting the construct with the cell-free extract preparation containing ribosomes under conditions effective for ribosome translation and the formation of a complex of the protein whose translation has been stalled, the mRNA encoding the protein, and the ribosomes. The protein in the complex is in a properly folded, active form and the complex is recovered.

Similar to the cell-based system described supra, the protein to be identified can be any ligand binding protein and the stall sequence is any sequence that interacts with residues in the ribosomal exit tunnel to stall translation. In a preferred embodiment, the ligand binding protein is a single chain antibody. Methods of making the construct comprising a deoxynucleic acid molecule encoding the protein of interest and the stall sequence are described supra.

Cell-free ribosome translation system are known in the art and have been successfully used for display and selection of a number of different binding molecules. See Mattheakis et al., "An In Vitro Polysome Display System for Identifying Ligands from Very Large Peptide Libraries," *PNAS* 91:9022-9026 (1994); Mattheakis et al., "Cell-Free Synthesis of Peptide Libraries Displayed on Polysomes," *Methods Enzymol* 267:195-207 (1996); Gersuk et al., "High-Affinity Peptide Ligands to Prostate-Specific Antigen Identifed by Polysome Selection," *Biochem Biophys Res Com* 232:578 582 (1997); Hanes and Pluckthun, "In Vitro Selection and Evolution of Functional Proteins by Using Ribosome Display," PNAS 94:4937-4942 (1997); Hanes et al., "Ribosome Display Efficiently Selects and Evolves High Affinity Antibodies In Vitro From Immune Libraries," *PNAS* 95:14130-50 (1998) which are all hereby incorporated by reference in their entirety. The protein-mRNA-ribosome complex can be recovered as described supra.

A primary advantage of using a cell-free translation system to achieve ribosome display is the ability to easily manipulate selection biases to enhance stability of the identified protein. As described supra, stability can generally be defined as the propensity of a molecule to exist in its folded and active state. A stability selection pressure may disrupt or prevent a polypeptide folding correctly such that it does not attain an active or fully active state. A stability selection pressure may affect the ability of a polypeptide to remain in its folded and active state. A stability selection pressure may differentiate in some way between polypeptides that are in a folded and active state and those that are not.

U.S. Published Patent Application No. 20070298430 to Buchanan et al., which is hereby incorporated by reference in its entirety, describes various stability selection pressures that can be utilized in the cell-free ribosome display system of the present invention. A stability selection pressure may be a chemical denaturant, such as urea, guanidine HCl (GuHCl) or thiocyanate, for example, sodium thiocyanate. A stability selection pressure may be a reducing agent, such as dithiothreitol (DTT), Tris[2-carboxyethyl]phosphine hydrochloride (TCEP), mercaptoethanol or glutathione. A stability selection pressure may be a physical denaturant, such as pH or temperature, in particular increased temperature. A selection pressure may be a protease or enzyme capable of degrading protein. A selection pressure may be depletion of chaperons or small molecule protein folding inhibitors. A stability selection pressure may be the use of hydrophobic interaction chromatography (HIC).

Hydrophobic interaction chromatography (HIC) is a technique for the separation of biomolecules based on differences in their surface hydrophobicity. HIC techniques have been used as a part of protein purification strategies as well as an analytical tool for the detection of protein conformational changes (reviewed in Queiroz et al., "Hydrophobic Interaction Chromatography of Proteins," *J. Biotech.* 87: 143-159 (2001), which is hereby incorporated by reference in its entirety. HIC is based on hydrophobic attraction between the HIC matrix and the protein molecules. The HIC matrix consists of small non-polar groups (butyl, octyl or phenyl) attached to a hydrophilic polymer backbone (e.g.

cross-linked dextran or agarose). Many proteins, generally considered to be hydrophilic, also have sufficient numbers of hydrophobic groups allowing interaction with the HIC matrix. HIC is sensitive enough to interact with non-polar groups normally buried within the tertiary structure of the protein but exposed due to incorrect folding. The strength of the interaction is dependent upon the type of matrix, type and concentration of salt, pH, additives, and temperature.

The present invention is suitable for a number of uses.

Firstly, it can be used to isolate stability-enhanced single-chain variable fragment (scFv) antibodies that are efficiently folded and functional in the bacterial cytoplasm in the absence of disulfide bonds (so-called "intrabodies"). Using the intracellular ribosome display method of the present invention, the cytoplasmic stability, and thus intracellular function, of an scFc can be enhanced 2-3 fold after only a single round of mutagenesis and selection.

Another use of the present invention involves isolation of functionally enhanced disulfide-bond containing antibody fragments. In addition to using wild type (wt) E. coli to isolate scFvs that were stable in the reducing cytoplasmic environment, a trxB gor host mutant strain (in which the redox potential of the cytoplasm favors the formation of disulfide bonds in proteins) is used to affinity- and/or stability-mature scFvs that are stalled and folded under oxidizing conditions.

The present invention can also be employed in the screening of naïve libraries for cytoplasmically functional proteins with specific binding affinity to a given target molecule: In addition to using this invention for the selection of proteins and antibody fragments from constructed libraries, the technology of the present invention is suited for the selection of intracellularly functional antibodies that bind a specific antigen target from naïve (i.e., not stemming from preimmunized cells) libraries.

Stability-enhancement/evolution of proteins under optimized cellular conditions can also be carried out with the present invention. Since stalled proteins undergo folding in the cytoplasm, it is relatively straightforward and inexpensive to optimize in vivo folding conditions by co-expressing potent molecular chaperones and/or isomerases. In this regard, the present invention can be used for protein engineering experiments (i.e. by random mutagenesis) under conditions where the cellular environment is tuned to better suit the specific folding requirements of a particular target protein.

The present invention can also be combined with in vitro/in vivo selection strategies for protein engineering via ribosome display. Since SecM17-mediated stalling was previously shown to operate in vitro, it is foreseeable that the SecM17-mediated antibody display strategy of the present invention could be performed akin to traditional in vitro ribosome display, in which all steps including transcription and translation are performed using a cell-free system. As a result, the need for transformation was eliminated, yielding extremely large (>10) antibody libraries. The flexibility afforded by SecM17-directed stalling inside and outside of living cells would allow for direct comparisons between the selection biases that arise in antibody engineering studies performed in vitro versus in vivo or, instead, would allow hybrid selection strategies where certain rounds of selection proceed in vitro while certain others are carried out in vivo.

The following examples illustrate various methods for compositions in the treatment method of the invention. The examples are intended to illustrate, but in no way limit, the scope of the invention.

EXAMPLES

Example 1—Bacterial Strains and Plasmids

E. coli strain BL21(DE3) was used throughout except for in vivo β-gal activation experiments where the E. coli 959 strain was used which carries the AMEF β-gal gene (Martineau et al., "Expression of an Antibody Fragment at High Levels in the Bacterial Cytoplasm," *J Mol Biol* 280:117-27 (1998), which is hereby incorporated by reference in its entirety). Plasmids encoding the SecM stall sequence fusions were constructed as follows. First, a 285-nucleotide segment of the secM gene containing the 17-amino acid stall sequence (FSTPVWISQAQGIRAGP (SEQ ID NO: 1)), plus additional downstream regions, was amplified from plasmid pNH21 by PCR using primers (5'-CTCATGGTCGACTTCAGCACGCCCGTCTGG-3' (SEQ ID NO: 5)) and (5'-CTCATGCTCGAGTTAAAGCTTCTGCGCAACTGTTGGGAAGC-3' (SEQ ID NO: 6)) to introduce a SalI restriction site at the 5' end and an XhoI-HindIII restriction site at the 3' end. This PCR product was SalI-XhoI digested and ligated into the same sites of pET28a (Novagen). Second, removal of the additional SecM downstream regions performed by introducing a HindIII restriction site immediately after the 17-residue stall sequence using site-directed mutagenesis (Stratagene QuikChange® Kit) and primers (5'-GGCATCCGTGCTGGCCCTAAGCTTCAACGCCTCACCTAACAA-3' (SEQ ID NO: 7) and 5'-GTTGTTAGGTGAGGCGTTGAAGCTTAGGGCCAGCACGGATGCC-3' (SEQ ID NO: 8)), followed by digestion with HindIII and self-ligation to yield pET-SecM. Third, scFv13 and scFv13-R4 were amplified by PCR from plasmids pPM163 and pPM163-R4, (Martineau et al., "Expression of an Antibody Fragment at High Levels in the Bacterial Cytoplasm," *J Mol Biol* 280:117-27 (1998), which is hereby incorporated by reference in its entirety) respectively, using primers (5'-GCGATGCCATGGCCGACTACAAGGACGATGACGACAAGGGAGCCGAGGT GCAGCTG-3' (SEQ ID NO: 9) and 5'-GCGATGGTCGACTGCGGCCCATTCAG-3' (SEQ ID NO: 10)) that introduce a FLAG epitope tag and an NcoI restriction site at the 5' end and a SalI restriction site at the 3' end of each scFv sequence. Each PCR product was digested with NcoI and SalI and ligated into NcoI-SalI-digested pET-SecM to yield the intermediate constructs pET-scFv13-SecM17' and pET-scFv13-R4-SecM17'. A SacI restriction site was inserted immediately before the SalI restriction site using QuikChange® and primers (5'-GGATCTGAATGGGGCCGCAGAGCTCGTCGACTT CAGCACGCC-3' (SEQ ID NO: 11) and 5'-GGCGTGCTGAAGTCGACGAGCTCTGCGGCCCCATTCAGA TCC-3' (SEQ ID NO: 12)). Next, a 6× his tag, thrombin recognition sequence, and an AGSAAGSG (SEQ ID NO: 13) linker was introduced by amplifying a 670-nucleotide fragment from plasmid pET28-NDPK-GFP that contained these sequence elements plus the downstream NDPK sequence. SacI and SalI restriction sites were introduced at the 5' and 3' ends, respectively, of this 670-nucleotide fragment during amplification using primers (5'-CTCATGGAGCTCCATCATCATCATCATCACAGCAGCGGCCTGGTGC-3' (SEQ ID NO: 14) and 5'-CTCATGGTCGACGCC AGAACCAGCAGCGG-3' (SEQ ID NO: 15)). This PCR product was SacI-SalI-digested and ligated into similarly digested pET-scFv13-SecM17' or pET-scFv13-R4-SecM17'. The additional NDPK sequence was excised by first inserting an EcoRI restriction site before the NDPK sequence using QuikChange® and primers (5'-GTGCCGCGCGGCAGCCATGAATTCATGCATGC- TATAAATATTGC-3' (SEQ ID NO: 16) and 5'-GCAATATT-TATAGCATGCATGAATTCATGGCTGCCGCGCGGCAC-3' (SEQ ID NO: 17)). A second EcoRI restriction site was inserted immediately after the NDPK sequence using the QuikChange® Kit and primers (5'-GAGGAGGTTTAGAG-GAATTCGGATCCGCTGGCTCCG-3' (SEQ ID NO: 18) and 5'-CGGAGCCAGCGGATCCGAATTCCTCTAAAAC-CTCCTC-3' (SEQ ID NO: 19)). Finally, excision of NDPK with EcoRI and self-ligation yield the final pET-scFv13-SecM17 and pET-scFv13-R4-SecM17 vectors (illustrated in FIG. 1). Plasmids encoding the unfused scFv sequences were constructed by amplifying the scFv13 (or the scFv13 variants R1, R2 and R4) sequence by PCR from plasmids pPM163, pPM163-R1, pPM163-R2, and pPM163-R4 (Martineau et al., "Expression of an Antibody Fragment at High Levels in the Bacterial Cytoplasm," *J Mol Biol* 280:117-27 (1998), which is hereby incorporated by reference in its entirety) with primers (5'-GCGATGCCATGGCCGACTA-CAAGGACGATGACGACAAGGGAGCCGAGGT GCA-GCTG-3' (SEQ ID NO: 20) and 5'-GCGATGGAGCTCT-TATGCGGCCCCATTCAG-3' (SEQ ID NO: 21)) that introduce a FLAG epitope tag and an NcoI restriction site at the 5' end and a SacI restriction site at the 3' end. This PCR product was digested with NcoI and SacI and ligated into similarly digested pET28a.

Example 2—Random Mutagenesis of scFv13 Sequence

A library of random mutants was constructed by error-prone PCR of the scFv13 gene sequence using pET-scFv13-SecM17 as template and skewing the nucleotide and magnesium concentrations as described (DeLisa et al., "Genetic Analysis of the Twin Arginine Translocator Secretion Pathway in Bacteria," *J Biol Chem* 277: 29825-31 (2002) and Fromant et al., "Direct Random Mutagenesis of Gene-Sized DNA Fragments Using Polymerase Chain Reaction," *Anal Biochem* 224:347-53 (1995), which are hereby incorporated by reference in their entirety) to generate a 1.5% error-rate library. Error-prone PCR products were amplified with using primers (5'GCGATGCCATGGCCGACTACAAGGAC-GATGACGACAAGGGAGCCGAG GTGCAGCTG-3' (SEQ ID NO: 22) and 5'-GCGATGGTCGACTGCGGC-CCCATTCAG-3' (SEQ ID NO: 23)), restriction digested with NcoI-SacI and ligated into the pET-scFv13-SecM17 that had previously been digested with NcoI-SacI to excise the wt scFv13 gene. Reaction mixtures were electroporated into E. cloni Express™ BL21(DE3) cells (Lucigen) and serial dilutions of these cells were plated on kanamycin (50 µg/ml) to determine the number of independent transformants. Transformed cells were selected on LB plates containing kanamycin (50 µg/ml). Library cells were pooled, cultured, and induced for scFv expression prior to isolation of ribosomes for panning and selection experiments.

Example 3—Cell Fractionation

Cells transformed with the pET28a-derived scFv constructs were grown in 10-ml cultures at 37° C. in Luria-Bertani (LB) supplemented with kanamycin (50 µg/ml). Protein synthesis was induced by adding 1 mM isopropyl-β-D-thiogalactopyranoside (IPTG) when cells reached to mid log phase ($OD_{600}$~0.5). Cells were harvested after 1 hour of induction and pelleted by centrifugation for 15 min at 4° C. and 3,500 rpm. The soluble fraction was prepared by resuspending the pellet in 300 ml of phosphate buffered saline (PBS) solution followed by sonication (Branson Sonifier). The sonicant was spun for 15 min at 4° C. and 1,300 rpm and the resulting supernatant was collected as the soluble fraction.

Example 4—Isolation of Ribosomes

Ribosomes were isolated according to a procedure modified from Evans et al., "Homogeneous Stalled Ribosome Nascent Chain Complexes Produced in vivo or in vitro," *Nat Methods* 2:757-62 (2005), which is hereby incorporated by reference in its entirety. Specifically, 100-ml cultures grown as above were induced with 1 mM IPTG at an OD600~0.5 and grown at 30° C. for an additional 30 min. Following expression, two Buffer C (20 mM Tris-HCl pH 7.5, 50 mM $NH_4Cl$, 25 mM $MgCl_2$) ice cubes were added to each culture flask, rapidly shaken for 1 min on ice, and incubated on ice for an additional 30 min. Next, cells were pelleted by centrifugation as above and resuspended in 600 µl of cold Buffer C. Cells were lysed by three cycles of freeze-thawing in liquid nitrogen followed by the addition of three 30-µl aliquots of lysozyme (Novagen), where the stock lysozyme solution was diluted 50 fold in cold Buffer C and each lysozyme addition was followed by a 20 min incubation at 4° C., and finally three additional freeze-thawing cycles. To reduce the viscosity of the lysates, three 12-µl aliquots of RQ1Dnase (Promega) were added and samples were rotated for 15 min at 4° C. after each dose of the enzyme. Samples were spun in a microcentrifuge for 20 min at 13,000 rpm at 4° C. to pellet the debris. To isolate ribosomes, the supernatant was collected and loaded onto a cold cushion made up of equal volumes of Buffer C supplemented with 5% sucrose phase and Buffer B (20 mM Tris-HCl pH 7.5, 500 mM $NH_4Cl$, 25 mM $MgCl_2$) supplemented with 37% sucrose phase. Ribosomes were isolated by ultracentrifugation for 35 h at 24,000 rpm and 4° C. using a Beckman LS 8 ultracentrifuge with an SW28 rotor. The crude ribosome pellet was resuspended in 200 µl Buffer C and ultracentrifuged in a 10 to 40% (w/v) sucrose gradient in Buffer A (20 nM Tris-HCl pH 7.5, 100 mM $NH_4Cl$, 25 mM $MgCl_2$) for 17 h at 22,000 rpm and 4° C. in a SW41 rotor. Gradient fractionation was performed manually by pipetting 250 µl at a time from the top part of the gradient. All collected samples were stored at 4° C. for further analysis.

Example 5—Affinity Selection of Ribosome Complexes, mRNA Isolation, and RT-PCR

A 96-well BD FALCON plate was coated with 65 µl of 1 mg/ml β-gal (Sigma) in PBS and left at 4° C. overnight. The plate was washed 4 times with 200 µl of PBS at room temperature and blocked with 200 µl of blocking solution (1% non-fat milk, 5 mM $MgCl_2$, 2.5 mg/ml heparin, 0.05 mg/ml E. coli tRNA in PBS) for 2 h at room temperature. After 4 washes with washing solution (0.1% Tween 20, 5 mM $MgCl_2$ in PBS), the plate was incubated at 4° C. for 15-20 min. Isolated 70S ribosome samples were mixed gently with equal volume of cold blocking solution, and 100 µl this mixture was added to each well. The plate was incubated for 1 h at 4° C. and washed 5-6 times with 200 µl of cold washing solution at 4° C. to remove any unbound complexes. mRNA was dissociated from ribosome complexes by adding 100 µl of cold eluting solution (20 mM EDTA, 20 units/ml RNAsin in PBS) to each well and shaking gently for 30 min at 4° C. Samples were collected into cold microcentrifuge tubes after scraping the plate surface with a tip to ensure complete sample removal. mRNA was purified using the RNEasy Purification Kit (Qiagen). Reverse transcription PCR on the recovered mRNA was performed using the Sensiscript RT Kit (Qiagen) and reverse primer 5'-GCGATGGAGCTCTTATGCGGC-CCCATTCAG-3' (SEQ ID NO: 24), which binds the 3' end of scFv13 and introduces a SacI restriction site and a stop codon. PCR amplification was performed in a second step with the same reverse primer and forward primer 5'-GCG-GCGATGCCATGGCCGACTACAAGGACGATGACGA-CAAGGGAGGATC CGCCGAGGTGCAGCTG-3' (SEQ ID NO: 25), which re-introduces a 5' FLAG tag and NcoI restriction site. The PCR product was NcoI-SacI digested and ligated into similarly digested pET28a or pTrc99A.

Example 6—Western Blotting

Figure 6:
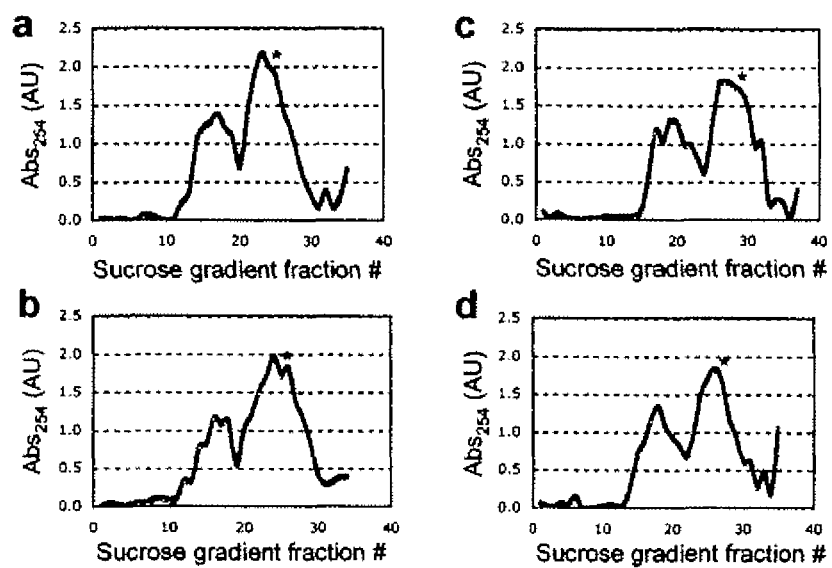
FIGS. 6A-D show the isolation of 70S ribosome fractions by sucrose density gradient centrifugation. The absorbance (254 nm) profile of gradient fractions shows accumulation of 70S ribosomes in fractions 23-28 (peak 70S-containing fraction indicated by asterisk). These figures show fractions generated from cells expressing: scFv13 (FIG. 6A); scFv13-R4 (FIG. 6B); scFv13-SecM17 (FIG. 6C); and scFv13-R4-SecM17 (FIG. 6D).

Cell lysates and ribosome fractions were resolved by SDS-PAGE using 12% Tris-HCl gels and immunoblotted according to a procedure modified from Chen et al, "Isolation of High-Affinity Ligand-Binding Proteins by Periplasmic Expression with Cytometric Screening (PECS)," *Nat Biotechnol* 19:537-42 (2001), which is hereby incorporated by reference in its entirety. To concentrate ribosome fractions for Western blot analysis, volumes of the collected ribosomal fractions were mixed with cold 20% (v/v) trichloroacetic acid (TCA) in a 1:2 volume ratio and allowed to precipitate for 30 min on ice. After centrifugation for 20 min at 35,000 rpm and 4° C., the pellet was dried of all remaining TCA and directly resuspended in 45 µl SDS-PAGE loading buffer. The following primary antibodies were used with the corresponding dilution in parenthesis: mouse anti-GroEL (1:10,000; Sigma); mouse anti-FLAG (1:1,500; Stratagene). The secondary antibodies were goat anti-mouse and goat anti-rabbit horseradish peroxidase conjugates (Promega) each diluted 1:10,000. Prior to Western blot analysis, a Bradford protein assay was performed on all samples to verify that an equal amount of total protein was loaded to each lane. In the cases where 70S ribosomal fractions were immunoblotted, fractions were normalized by rRNA content as measured by $OD_{260}$ (see FIG. 6). To verify the quality of subcellular fractions, membranes were first probed with primary antibodies and, following development, stripped in Tris-buffered saline supplemented with 2% SDS and 0.7 M β-mercaptoethanol. Stripped membranes were reblocked and probed with anti-GroEL antibody.

Example 7—ELISA

Cell lysates and ribosome samples were analyzed by ELISA according to the same steps described above for ribosome panning with the following modifications: (1) plates were coated with 100 µl of 10 µg/ml β-gal (Sigma) in PBS; and (2) 0.5% BSA was used instead of non-fat milk in the blocking solution. Following the washes after the samples were applied, instead of sample elution, 50 µl of anti-FLAG antibody (Stratagene) at a 1:5,000 dilution in blocking solution was added to each well and incubated for 1 h at 4° C. This was followed by four washes with cold washing solution and 1 h incubation at 4° C. with 50 µl of anti-mouse secondary antibody (Promega) at a 1:2,500 dilution in blocking solution. After four additional washes, bound scFvs were detected using SigmaFAST o-Phenylenediamine (OPD) tablets. The same procedure was followed for ELISA of protein samples, except that all steps were carried out at room temperature and in the absence of tRNA, heparin, and $MgCl_2$.

Example 8—Intracellular AMEF β-gal Activation

Strain AMEF 959 (Martineau et al., "Expression of an Antibody Fragment at High Levels in the Bacterial Cytoplasm," *J Mol Biol* 280:117-27 (1998), which is hereby incorporated by reference in its entirety) was transformed with each scFv13 variant encoded in plasmid pTrc99A. Six replicate colonies of each transformant were grown overnight in 200-µl cultures at 37° C. in a 96-well plate containing LB supplemented with 100 µg/ml ampicillin. 20 µl were subcultured into 200 µl fresh LB supplemented with 100 µg/ml ampicillin and 1 mM IPTG and induced for 6-8 hours at 37° C. until cells reached stationary phase. After induction, β-gal activity was measured using a whole cell assay modified from Arnold et al., "Influences of Transporter Associated with Antigen Processing (TAP) on the Repertoire of Peptides Associated With the Endoplasmic Reticulum-Resident Stress Protein gp96," *J Exp Med* 186:461-6 (1997), which is hereby incorporated by reference in its entirety. Specifically, 5-bromo-4-chloro-3-indolyl-β-D-galactopyranoside (X-gal) was added in each well to a final concentration of 1 mM and absorbance at 620 nm was recorded over 4-10 h at 37° C. to measure active β-gal.

Example 9—Behavior of an scFv Upon Fusion to SecM Stall Sequence

To create stalled ribosome complexes bearing recombinant scFv sequences for intracellular ribosome display, human scFv13 was chosen as a model. This was originally isolated by Winter and coworkers in a two-step procedure: first, in vitro phage display was used to isolate scFv binders to native *E. coli* β-galactosidase; second, isolated binders were evaluated for in vitro activation of a normally inactive β-galactosidase variant known as AMEF β-gal (Martineau et al., "Expression of an Antibody Fragment at High Levels in the Bacterial Cytoplasm," *J Mol Biol* 280:117-27 (1998), which is hereby incorporated by reference in its entirety). However, when scFv13 was tested for in vivo activation, it was only able to weakly activate AMEF, presumably because of the poor folding of the scFv fragment in the reducing *E. coli* cytoplasm. To remedy this situation, a directed evolution strategy was used to uncover scFv13 variants that exhibited increased activation of AMEF in vivo. This resulted in the isolation of clones scFv13-R1, -R2, -R3 and -R4, where the number designation refers to the round of mutagenesis and selection in which the variant was isolated (Martineau et al., "Expression of an Antibody Fragment at High Levels in the Bacterial Cytoplasm," *J Mol Biol* 280:117-27 (1998), which is hereby incorporated by reference in its entirety). The improved activation observed for these variants was found to arise in part from an increase in soluble cytoplasmic expression in the absence of disulfide bond formation.

Figure 2:
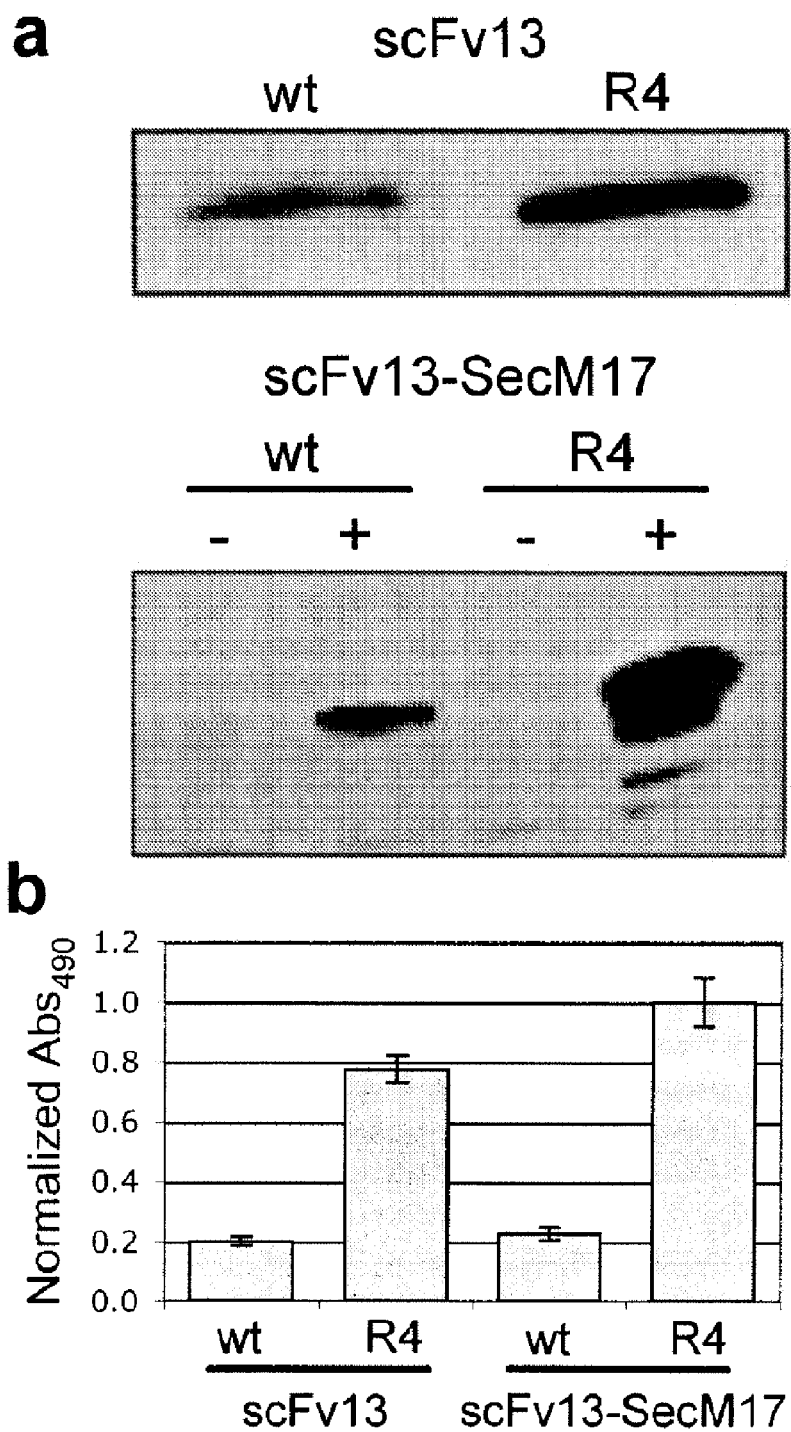
FIGS. 2A-B show the in vivo expression of scFv-SecM17 fusion proteins, in accordance with the present invention.

In the present studies, an expression plasmid that enabled fusions between scFv13 (or the scFv13-R4 clone) and the 17-amino acid SecM stall sequence (SecM17; see FIG. 1*b* and Methods) was first generated. The linker sequence between the scFv and SecM17 was designed to be sufficiently long so that scFvs would be fully exposed from the ribosome exit tunnel. Following expression of unfused or SecM17-fused versions of scFv13 and scFv13-R4 in wild-type (wt) *E. coli* cells, the soluble lysate was harvested and resolved using SDS-PAGE and Western blotting using an anti-FLAG monoclonal antibody specific for the N-terminal FLAG epitope tag on each scFv (FIG. 1B). Consistent with earlier reports (Martineau et al., "Expression of an Antibody Fragment at High Levels in the Bacterial Cytoplasm," *J Mol Biol* 280:117-27 (1998), which is hereby incorporated by reference in its entirety), a much greater quantity of soluble scFv13-R4 accumulated in the cytoplasm relative to wt scFv13 (FIG. 2A, upper panel); this difference in solubility was maintained when each scFv was expressed as a fusion to SecM17 (FIG. 2A, lower panel). To determine whether the scFv13-SecM17 fusion proteins were capable of binding their cognate antigen, an ELISA was performed with β-gal-coated plates. The scFv13-R4-SecM17 construct was found to bind β-gal at a level that was comparable to the unfused scFv13-R4 (FIG. 2B), whereas both versions of the much less soluble wt scFv13 (unfused and SecM17 fusion) gave ELISA signals that were only weakly above background. Thus, a direct comparison between scFv-SecM17 fusions and their unfused scFv counterparts revealed that folding and antigen binding were relatively unaffected by the attachment of the SecM stall sequence.

Figure 3:
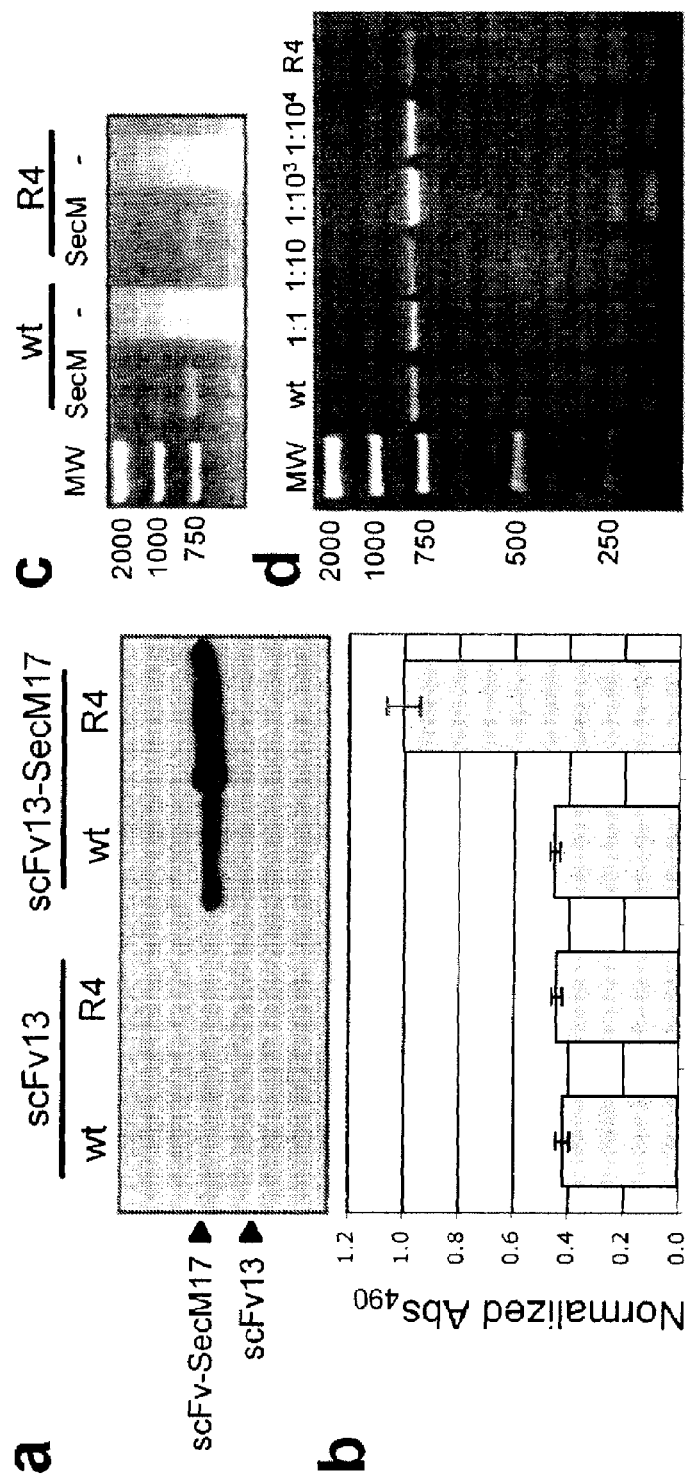
FIGS. 3A-D show that antibody fragments and mRNA are ribosome-associated. Western blot analysis (FIG. 3A) and ELISA (FIG. 3B) of 70S ribosome fractions were prepared from cells expressing the unfused or SecM17-fused scFv constructs (wt and R4) as indicated. An equivalent amount of total protein was loaded in each lane or analyzed in each ELISA plate well. For ELISA, absorbance values for each sample were normalized to the absorbance measured for the ribosome fraction isolated from scFv13-R4-SecM17-expressing cells. Data is the average of three replicate experiments, and the error bars represent the standard error of the mean. Agarose gel electrophoresis of PCR products generated from dissociated ribosomes corresponding to: unfused (—) and fused (SecM) versions of wt scFv13 (wt) and scFv13-R4 (R4) as indicated (FIG. 3C); and mixtures of wt scFv13-SecM17 and scFv13-R4-SecM17 ARM complexes according to the ratios indicated (FIG. 3D). Values given for MW marker bands indicate number of base pairs. The intensity of bands is due to efficiency of mRNA isolation and RT-PCR reaction and does not necessarily reflect relative abundance of mRNA.

Example 10—SecM17-Mediated Display of Functional scFvs on Stalled Ribosome Complexes Previous studies by Clark and colleagues indicated that SecM17-directed stalling resulted in stable translation-arrest of heterologously expressed phage P22 tailspike protein and green fluorescent protein on ribosome complexes in intact cells (Evans et al., "Homogeneous Stalled Ribosome Nascent Chain Complexes Produced in vivo or in vitro," *Nat Methods* 2:757-62 (2005), which is hereby incorporated by reference in its entirety). To determine whether scFv13-SecM17 fusions were functionally displayed on ribosomes in a similar manner, 70S ribosomes were isolated (see FIG. 6) from soluble proteins and other cell lysate components by sucrose cushion centrifugation. Following Western blotting, both scFv13-SecM17 fusions were detected in ribosome preparations whereas unfused seFv13 and scFv13-R4 were completely absent from identically prepared ribosome fractions (FIG. 3A), confirming that SecM17 is able to mediate the display of each scFv on intact ribosomes and that co-elution of scFvs with ribosomes depends on the presence of the SecM stall sequence. Consistent with the cell lysate expression data, the solubility-enhanced scFv13-R4-SecM17 construct was enriched in ribosome fractions relative to the scFv13-SecM17 construct (FIG. 3A), indicating that the amount of stalled molecules correlates with the solubility of the displayed scFv. Moreover, only stalled ribosome complexes displaying the more soluble scFv13-R4-SecM17 construct were observed to strongly bind β-gal over background; scFv13-SecM17 constructs yielded only a low level of binding activity above background (FIG. 3B).

It is noteworthy that the growth rates of cells expressing unfused scFvs or scFv13-SecM17 fusions were indistinguishable from the growth rate of empty vector control cells during the 30-90 min induction period. To determine if SecM17-mediated stalling of scFvs had a more subtle influence on natural cellular processes such as chaperone binding to the ribosome, ribosome preparations were probed for the presence of trigger factor (TF) which is known to dock on the ribosome near the exit tunnel (Kramer et al., "L23 Protein Functions as a Chaperone Docking Site on the Ribosome," *Nature* 419:171-4 (2002), which is hereby incorporated by reference in its entirety). Western blotting of ribosome fractions using anti-TF serum revealed that similar amounts of TF were associated with ribosomes from cells expressing either the unfused scFv13-R4, the stalled scFv13-R4-SecM17 construct or an empty vector control, indicating that SecM17-arrested proteins do not prevent TF binding to ribosomes.

Example 11—Genotype to Phenotype Link on Stalled Ribosome Complexes

While previous studies demonstrated efficient SecM17-directed stalling on ribosomes (Evans et al., "Homogeneous Stalled Ribosome Nascent Chain Complexes Produced in vivo or in vitro," *Nat Methods* 2:757-62 (2005), which is hereby incorporated by reference in its entirety), it was not determined whether intact mRNA remained associated with these stalled complexes. Thus, it was next tested whether SecM17 stalling resulted in stable ARM complexes and, if so, whether ribosome-associated mRNA remained intact during in vivo display in the presence of cellular RNAses and during recovery. Ribosome fractions prepared from cells expressing either scFv13 or scFv13-R4 in an unfused or SecM17-fused format were incubated with immobilized β-gal and bound ribosome complexes were dissociated with EDTA. Ribosome-associated RNA, including stalled mRNA, was isolated from dissociated complexes and the mRNA encoding the scFv13 sequence was amplified using RT-PCR using general primers that annealed to both scFv13 and scFv13-R4. Remarkably, ribosome fractions corresponding to unfused scFvs yielded no distinct PCR bands whereas both the scFv13-SecM17 and the solubility-enhanced scFv13-R4-SecM17 constructs gave rise to a substantial PCR product corresponding in size to the full-length scFv13 sequence (FIG. 3C); sequencing of each PCR product identified these as the wt scFv13 and scFv13-R4 mRNA sequences, respectively. The fact that mRNA was recovered from ribosomes displaying wt scFv13 is consistent with the fact that antigen binding activity for these ARM complexes was detected above background, albeit at a much weaker level relative to ribosomes displaying scFv13-R4 (see FIG. 3B). Collectively, these data confirm that the model scFv used in these experiments and its encoding mRNA remain stably attached to stalled ribosomes thereby connecting genotype to phenotype in a manner that is amenable to engineering of antibody fragments in vivo.

Example 12—Specific Enrichment of Solubility-Enhanced scFvs Displayed on Stalled Ribosomes To evaluate the potential of the system of the present invention for uncovering rare clones from a very large excess of background, solubility-enhanced scFv13-R4 isolation from a moderate excess of the less soluble scFv13 was attempted. Mixtures of stalled ribosomes generated from cells expressing the scFv13-SecM17 and scFv13-R4-SecM17 constructs were panned on β-gal and, following competitive binding, a PCR product was generated from the dissociated ARM complexes using general primers that could amplify both scFv13 and seFv13-R4. PCR products were ligated into an expression plasmid that was transformed into *E. coli* and 10 randomly selected single clones were analyzed for each mixture to determine the identity of the plasmid-encoded scFv. In mixtures containing wt scFv13-SecM17 stalled ribosome complexes at an excess, over scFv13-R4-SecM17 ARM complexes, of 10:1, 100:1, 1,000:1 or 10,000:1, the solubility-enhanced scFv13-R4 sequence was recovered 100% of the time after only a single round of selection (representative PCR products for these cases are shown in FIG. 3D). The mRNA from the wt sequence was only recovered when samples containing wt scFv13 ARM complexes were panned alone on β-gal (i.e., in the absence of any R4 complexes; FIG. 3D, lane 1). Thus, even though the weakly active wt scFv13 could be recovered during the panning procedure, highly soluble scFv13-R4 easily out competed wt scFv13 during competitive binding experiments; hence only the most soluble and most active antibody fragments are efficiently and preferentially selected using SecM17-directed ribosome display.

Example 13—Stability Maturation of scFv13 Via SecM17-Mediated Intracellular Display To test whether the present intracellular display strategy allowed stability-maturation of scFvs, a complete cycle of mutagenesis and screening (see FIG. 1A) was performed to improve the solubility of wt scFv13. A diverse library of the wt scFv13 was generated by error-prone PCR under conditions that resulted in an error rate of ~1.0% nucleotide substitutions per gene (DeLisa et al., "Genetic Analysis of the Twin Arginine Translocator Secretion Pathway in Bacteria," *J Biol Chem* 277: 29825-31 (2002) and Fromant et al., "Direct Random Mutagenesis of Gene-Sized DNA Fragments Using Polymerase Chain Reaction," *Anal Biochem* 224:347-53 (1995), which are hereby incorporated by reference in their entirety) as determined by sequencing 20 randomly selected library clones. The resulting error-prone PCR product was ligated in-frame with the SecM stall sequence and, following transformation, a cell library containing ~$5 \times 10^6$ transformants was obtained. Members of this cell library were induced and ribosome fractions were prepared and screened by panning on immobilized β-gal to isolate clones exhibiting enhanced solubility relative to wt scFv13. A total of twelve unique clones were obtained after only a single round of selection and each was evaluated in an unfused format (i.e., lacking the SecM stall sequence in pET28a) for soluble expression and antigen binding. Of the twelve clones tested, 10 clones exhibited levels of soluble expression as measured by Western blotting and levels of activity as measured by ELISA that were comparable or slightly improved compared to wt scFv13. However, two clones were isolated, namely S20 and S23, that exhibited soluble expression levels that were dramatically increased over wt scFv13 (FIG. 4A) and comparable to the solubility-enhanced clones scFv13-R1 and seFv13-R2 clones isolated previously by Winter and colleagues following one and two rounds of mutagenesis and selection, respectively (Martineau et al., "Expression of an Antibody Fragment at High Levels in the Bacterial Cytoplasm," *J Mol Biol* 280:117-27 (1998), which is hereby incorporated by reference in its entirety). To test whether the improved solubility of clones S20 and S23 was sufficient to render each scFv functional in the cytoplasm, the ability of S20 and S23 to activate AMEF β-gal in vivo was tested. This first required subcloning of each scFv into plasmid pTrc99A since the host strain required for AMEF β-gal activation assays was not a DE3 lysogen and thus incompatible with T7-mediated pET28a expression. Soluble expression of S20 and S23 from pTrc99A showed a greater than 2.0- and 1.5-fold improvement, respectively, over wt scFv13 as determined by densitometry (FIG. 4B). Upon cytoplasmic expression of clones S20 and S23 in *E. coli* cells carrying a chromosomal copy of the mutant AMEF 959 β-gal gene instead of wt β-gal, (Martineau et al., "Expression of an Antibody Fragment at High Levels in the Bacterial Cytoplasm," *J Mol Biol* 280: 117-27 (1998), which is hereby incorporated by reference in its entirety) increase levels of in vivo activation were observed that were approximately 2-fold greater than wt scFv13 and on par with the activation conferred by clones scFv13-R1 and scFv13-R2 (FIG. 4C) isolated previously (Martineau et al., "Expression of an Antibody Fragment at High Levels in the Bacterial Cytoplasm," *J Mol Biol* 280: 117-27 (1998), which is hereby incorporated by reference in its entirety).

Figure 5A:
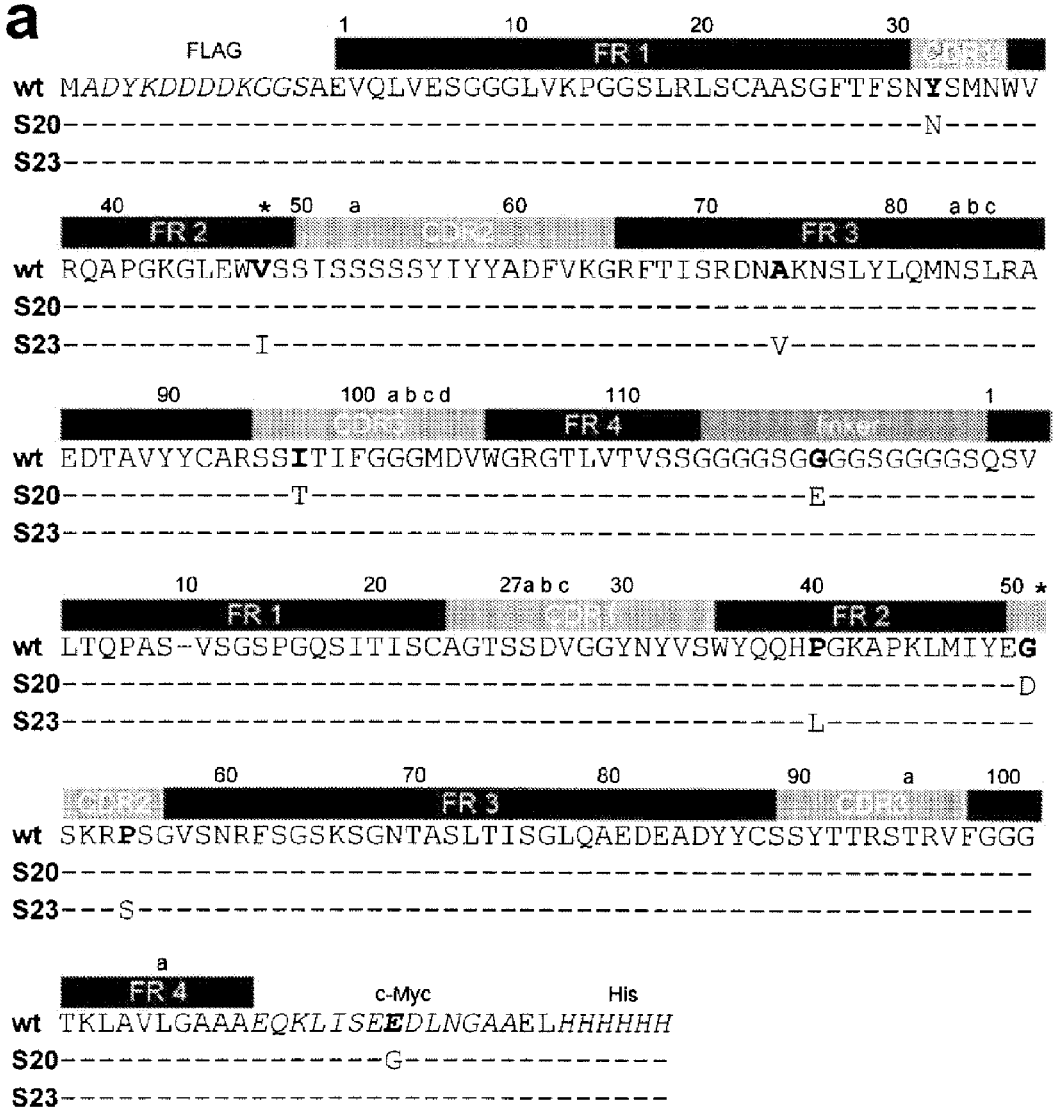
FIGS. 5A-B show the mutations in scFv13 fragments selected by intracellular ribosome display.
Figure 5B:
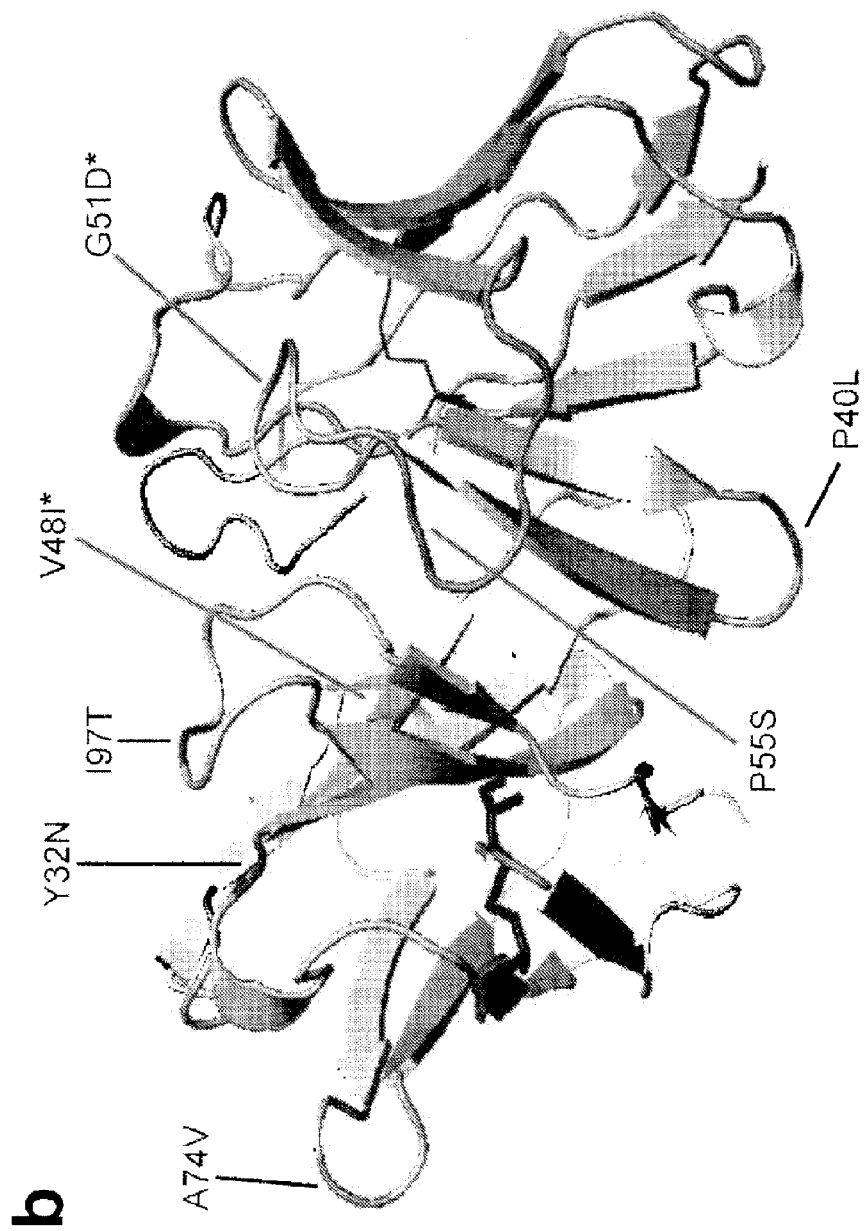

While none of the present clones shared mutations with these previously isolated early round clones, it is particularly noteworthy that both clones S20 and S23 (but none of the other 10 isolated clones) carried mutations that were also present in the solubility-enhanced clone scFv13-R4. These were G51D in $V_L$ of S20 and V48I in $V_H$ of S23 (FIG. 5A). In addition, S20 and S23 both carried at least one mutation in their complementary determining regions (CDRs): Y32N (CDR1) and 197T (CDR3) in $V_H$ of S20 and P55S (CDR2) in $V_L$ of S23 (FIG. 5A). This might contribute in part to the improved β-gal binding observed in vitro and in vivo. Further analysis of the location of the mutated residues on a three-dimensional model of scFv13 revealed that 3 out of 3 mutations in S20 and 3 out of 4 mutations in S23 were located in surface-exposed loops or turns of the structure (FIG. 5B). Although inspection of this structural model is insufficient to fully elucidate the contribution of these mutations to improved cytosolic stability, their location is interesting given the common observation that mutations that reduce aggregation are often (but not always) located in loops and turns on a protein's surface (Martineau et al., "Expression of an Antibody Fragment at High Levels in the Bacterial Cytoplasm," *J Mol Biol* 280:117-27 (1998), which is hereby incorporated by reference in its entirety).

The 17-residue SecM stall sequence has been shown to be sufficient to mediate stalling of scFvs in vivo and gives rise to ARM complexes. Stalling was found to be stable and relatively long-lived as the quantity of stalled ribosome complexes bearing scFvs was similar following induction periods of 30-90 min. Translation-arrested scFvs displayed on ribosomes retained the folding and antigen binding characteristics of the unfused scFvs from which they were derived and did not appear to affect cellular physiology (there was no significant change in cell growth rate following induction of scFv-SecM17 chimeras) or binding of ribosome-associated chaperones. This suggests that SecM17-mediated stalling might prove to be a useful tool for studying the interaction between stalled nascent chains and the ribosomal exit tunnel or exit tunnel-associated chaperone systems (e.g., TF). Importantly, because the scFv and its encoding mRNA remain stably associated with ribosomes, a link between genotype and phenotype is created in vivo that makes this method ideally suited for directed antibody evolution. Moreover, since scFv stalling and folding occur inside intact cells, this method naturally selects for scFvs that are solubly expressed in the normally reducing cytoplasm of *E. coli*. Consistent with this notion, it was shown that from a diverse library of scFv sequences fused to the SecM stall sequence, solubility-enhanced proteins could be isolated in a single round of mutagenesis and selection. Two (out of 12 selected clones) not only showed strong binding to their antigen, β-gal, but also activated a non-functional variant of β-gal in the cytoplasm of intact cells as a result of their improved solubility (and perhaps affinity), demonstrating the potential of this method for engineering intracellular antibodies (Cattaneo et al., "The Selection of Intracellular Antibodies," *Trends Biotechnol* 17:115-21 (1999), which is hereby incorporated by reference in its entirety).

Figure 4:
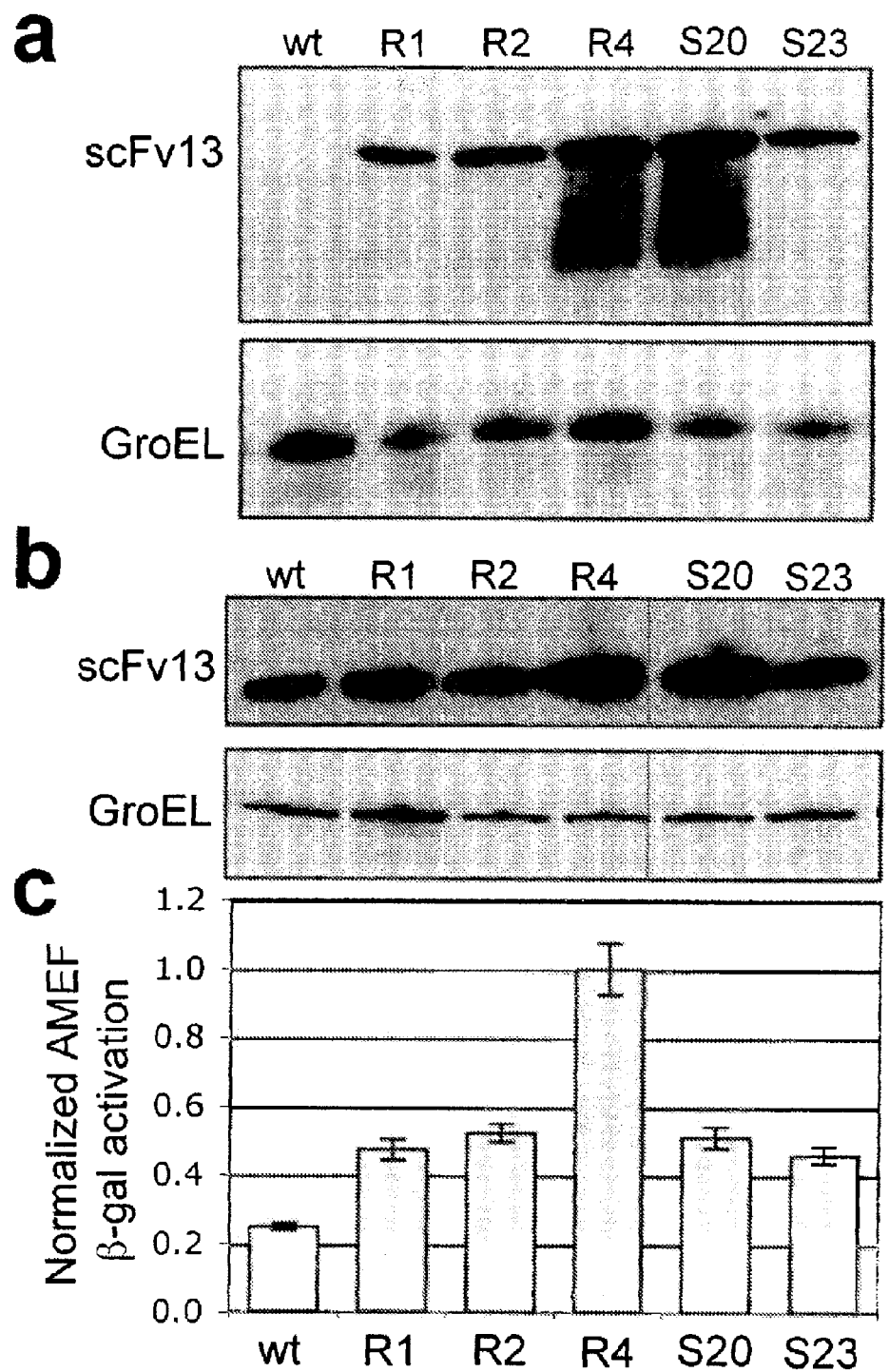
FIGS. 4A-C show the solubility and binding activity of selected scFv13 fragments. Western blot analysis was conducted for soluble fractions recovered from BL21(DE3) cells expressing unfused versions of scFv13 and related variants from plasmid pET28a (FIG. 4A) and pTrc99A (FIG. 4B). Clones scFv13-R1, scFv13-R2, and scFv13-R4 were isolated previously after 1, 2, and 4 rounds of evolution, respectively (Martineau, et. al., "Expression of an Antibody Fragment at High Levels in the Bacterial Cytoplasm," *J. Mol. Biol.* 280: 117-27 (1998), which is hereby incorporated by reference in its entirety). Clones S20 and S23 represent the two best clones isolated in this study after a single round of mutagenesis. Note that expression of all scFvs from pTrc99A was lower relative to expression from pET28a, however sample volumes and development time for pET28a blots were 4-fold and 10-fold reduced, respectively, relative to pTrc99A blots. An equivalent amount of total protein was loaded in each lane of FIGS. 4A and 4B. Blots were first probed with anti-FLAG IgG and, following stripping, reprobed with anti-GroEL IgG. GroEL serves as a marker to confirm equivalently loaded samples.

As is clearly evident in FIG. 4, the clones of the present invention compare quite favorably with scFv13 clones R1 and R2 that were isolated by Martineau et al., "Expression of an Antibody Fragment at High Levels in the Bacterial Cytoplasm," *J Mol Biol* 280:117-27 (1998), which is hereby incorporated by reference in its entirety, following one and two rounds of mutagenesis and selection, respectively. The inability to isolate an R4 (or R4-like clone), despite the very dramatic single-round enrichment of this clone in the test case mimicking a library, is suspected to stem from the fact that laboratory evolution, like natural evolution, is typically a gradual process; hence, the clones isolated via just a single round of evolution. Thus, the fact that the S20 and S23 clones had comparable solubility and activity to scFv13-R1 and scFv13-R2 and that these clones both carried mutations that were found in scFv13-R4, suggests that applicants were on a similar evolutionary trajectory. Furthermore, since R4 was dramatically enriched over wt scFv13 artificial library experiments, additional rounds of mutagenesis and selection using the present assay should yield clones on par with R4 (that is, the present assay is far from saturation). Not surprisingly, 10 isolated clones did not show any major solubility and activity improvement over the wt sequence after one round of evolution. This can be explained by the fact that poorly expressed and/or weak binders (like wt scFv13) that can form stable ARM complexes with some degree of binding to β-gal can likely be recovered in the absence of really strong binders like clone R4. This is consistent with the fact that evolution experiments performed by traditional in vitro display (e.g., phage, ribosome) begin to show enrichment for clones with significant affinity enhancement only after several rounds of evolution, when presumably stronger clones begin to arise that can completely out compete the less fit clones that are initially in excess. Alternatively, it may be that these 10 clones are more soluble and/or tighter binders in the context of SecM17 but lose these characteristics when expressed in an unfused format. Indeed, proteins displayed on ribosomes are less prone to aggregation, perhaps because association with ribosomes is likely to have solubility-enhancing effects (Lipovsek et al., "In vitro Protein Evolution by Ribosome Display and mRNA Display," *J Immunol Methods* 290:51-67 (2004) and Sorensen et al., "Soluble Expression of Aggregating Proteins by Covalent Coupling to the Ribosome," *Biochem Biophys Res Commun* 319:715-9 (2004), which are hereby incorporated by reference in their entirety). Thus, like with any assay for improving protein folding based on a fusion reporter construct (e.g., GFP (Waldo et al., "Rapid Protein-Folding Assay Using Green Fluorescent Protein," *Nat Bioteehnol* 17:691-5 (1999), which is hereby incorporated by reference in its entirety) or β-lactamase (Fisher et al., "Genetic Selection for Protein Solubility Enabled by the Folding Quality Control Feature of the Twin-Arginine Translocation Pathway," *Protein Sci* 15:449-58 (2006), which is hereby incorporated by reference in its entirety)), care must be taken to validate all positive hits in the absence of the fusion partner.

Importantly, because the functional selection involved in the present method depends only on the binding ability of the target scFv to an antigen that has been immobilized in vitro, the present intracellular display strategy is suitable to isolate any stability-enhanced antibody with binding affinity for any antigen (not limited to β-gal). The only requirements, which are the same for traditional in vitro ribosome display, are that the antibody fragment must be amenable to display in the context of ARM complexes and that the binding target is known and available in a purified form to allow for selection. In this study, the human antibody fragment (scFv13) represented an attractive model protein owing to its ability to function as an intrabody; hence, solubility improvement accomplished using the present assay could be conveniently verified by monitoring activation of a β-gal mutant (AMEF) in vivo. It should be noted, however, that the present selection procedure to interrogate scFv13 error-prone library members was entirely independent of this cytoplasmic activity assay. In fact, the simplest measures of improved performance of an antibody evolved using this system are: (i) solubility as determined by Western blotting of the soluble fraction; and (ii) function as determined by ELISA. Thus, the engineering of functional intrabodies is only one potential application of the present system. Indeed, a more likely application of this technology will be solubility enhancement of poorly expressed antibody fragments whose targets are conventional extracellular antigens. Such experiments could be performed in either a reducing or, perhaps more appropriately, in a non-reducing (e.g., strain FÅ113 having an oxidizing cytoplasm (Bessette et al., "Efficient Folding of Proteins With Multiple Disulfide Bonds in the *Escherichia coli* Cytoplasm," *Proc Natl Acad Sci USA* 96:13703-8 (1999), which is hereby incorporated by reference in its entirety) strain background.

The recent observation of nascent peptide-mediated translation arrest on eukaryotic ribosomes (Onouchi et al., "Nascent Peptide-Mediated Translation Elongation Arrest Coupled With mRNA Degradation in the CGS1 Gene of *Arabidopsis*," *Genes Dev* 19:1799-810 (2005), which is hereby incorporated by reference in its entirety) highlights the potential for using intracellular ribosome display to engineer proteins directly in the cytoplasm of eukaryotic cells. Moreover, since SecM17-mediated stalling was previously shown to operate in vitro (Evans et al., "Homogeneous Stalled Ribosome Nascent Chain Complexes Produced in vivo or in vitro," *Nat Methods* 2:757-62 (2005), which is hereby incorporated by reference in its entirety), it is foreseeable that the present SecM17-mediated antibody display strategy could be performed akin to traditional in vitro ribosome display (Hanes et al., "In vitro Selection and Evolution of Functional Proteins by Using Ribosome Display," *Proc Natl Acad Sci USA* 94:4937-42 (1997) and Mattheakis et al., "An in vitro Polysome Display System for Identifying Ligands from Very Large Peptide Libraries," *Proc Natl Acad Sci USA* 91:9022-6 (1994), which are hereby incorporated by reference in their entirety), in which all steps including transcription and translation are performed using a cell-free system thereby eliminating the need for transformation and, as a result, yielding extremely large (>$10^{10}$) antibody libraries (Hanes et al., "Ribosome Display Efficiently Selects and Evolves High-Affinity Antibodies in vitro from Immune Libraries," *Proc Natl Acad Sci USA* 95:14130-5 (1998), which is hereby incorporated by reference in its entirety). The flexibility afforded by SecM17-directed stalling inside and outside of living cells would allow for direct comparisons between the selection biases that arise in antibody engineering studies performed in vitro versus in vivo or, instead, would allow hybrid selection strategies where certain rounds of selection proceed in vitro while certain others are carried out in vivo. Aside from providing a complement to traditional in vitro ribosome display (Hanes et al., "In vitro Selection and Evolution of Functional Proteins by Using Ribosome Display," *Proc Natl Acad Sci USA* 94:4937-42 (1997) and Mattheakis et al., "An in vitro Polysome Display System for Identifying Ligands from Very Large Peptide Libraries," *Proc Natl Acad Sci USA* 91:9022-6 (1994), which are hereby incorporated by reference in their entirety), intracellular ribosome display offers a number of advantages. For instance, expression and stalling of proteins on ribosomes is less technically challenging as these steps are performed entirely inside cells, requiring only an inducer (e.g., IPTG) to initiate the entire process from start to finish. Also, bacterial cell culture, but not cell-free translation, can be easily scaled to produce large quantities and high concentrations of stalled ribosome complexes that might be necessary for various applications such as making biophysical measurements using NMR. Since stalled scFvs undergo folding in the cytoplasm, it is relatively straightforward and inexpensive to optimize in viva folding conditions by co-expressing potent molecular chaperones and/or isomerases (Jurado et al, "Production of Functional Single-Chain Fv Antibodies in the Cytoplasm of *Escherichia coli,*" *J Mol Biol* 320:1-10 (2002) and Levy et al., "Production of Correctly Folded Fab Antibody Fragment in the Cytoplasm of *Escherichia coli* trxB gor Mutants via the Coexpression of Molecular Chaperones," *Protein Expr Purif* 23:338-47 (2001), which are hereby incorporated by reference in their entirety) and by employing engineered *E. coli* strains such as trxB gor mutants in which the redox potential of the cytoplasm favors the formation of disulfide bonds in proteins (Bessette et al., "Efficient Folding of Proteins With Multiple Disulfide Bonds in the *Escherichia coli* Cytoplasm," *Proc Natl Acad Sci USA* 96:13703-8 (1999), which is hereby incorporated by reference in its entirety). While wt *E. coli* were used in this study to isolate scFvs that were stable in the reducing cytoplasmic environment, one could employ a trxB gor host strain to affinity- and/or stability-mature scFvs that are stalled and folded under oxidizing conditions. Either way, scFv proteins enriched by intracellular ribosome display are naturally predisposed for in vivo expression and function. In contrast, those enriched by in vitro ribosome display often do not express well in vivo and thus require refolding from inclusion bodies (Hanes et al., "Ribosome Display Efficiently Selects and Evolves High-Affinity Antibodies in vitro from Immune Libraries," *Proc Natl Acad Sci USA* 95:14130-5 (1998), which is hereby incorporated by reference in its entirety) which can be laborious and time-consuming. Finally, while not demonstrated here, it would be desirable in the future to perform the entire ribosome display process inside living cells, from translation to stalling to antigen panning; such a strategy would eliminate the need for antigen purification and immobilization and would enable direct selection of intracellular antibodies that fold and function in the cytoplasm. Such a strategy would also reduce the likelihood of false positives that may arise due to undesired antibody folding upon removal of ARM complexes from the cytoplasmic environment prior to the panning procedure. Currently, this is regulated by instantaneous cooling of the ARM complexes to 4° C. (where the kinetics of folding are extremely slow) and by performing the biopanning step immediately after complexes are isolated. Moreover, the ability to display a functional binding protein on ribosomes and simultaneously express its interacting partner could potentially be used to engineer and even block protein-protein interactions inside cells. Taking together all the aforementioned advantages, intracellular ribosome display is a powerful complementary method to in vitro ribosome display for the directed evolution of proteins and should find use in the engineering of potent binding proteins that are soluble inside host cells for applications in functional genomics and proteomics as well as molecular medicine.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

---

What is claimed:

1. A method comprising:
providing a construct comprising a deoxyribonucleic acid molecule encoding a protein which binds to a target molecule, said deoxyribonucleic acid molecule being coupled to a stall sequence;
transforming a host cell with the construct;
culturing the host cell under conditions effective to form a complex within the host cell, the complex comprising the protein whose translation has been stalled, an mRNA encoding the protein, and ribosomes, wherein the protein in the complex is in a properly folded, active form;
recovering the complex from the cell; and
isolating the mRNA from the recovered complex.

2. The method of claim 1 further comprising:
reverse transcribing the isolated mRNA to form a cDNA encoding the protein;
forming a construct comprising the cDNA coupled to the stall sequence; and
repeating said transforming, said culturing, and said recovering to enrich the protein recovered.

3. The method of claim 1, wherein said isolating comprises:
dissociating the complex.

4. The method of claim 3, wherein said dissociating is carried out with EDTA.

5. The method of claim 2 further comprising:
characterizing enrichment of the protein by sequencing or ELISA.

6. The method of claim 2, wherein said isolating, said reverse transcribing, said forming, and said repeating are carried out multiple times.

7. The method of claim 1, wherein the stall sequence is SecM coupled to the deoxyribonucleic acid molecule.

8. The method of claim 7, wherein the construct further comprises:
an epitope flag,
a c-Myc epitope tag,
a 6x-His tag,
a thrombin cleavage site,
a linker, and
a stop codon; wherein the c-Myc epitope tag, the 6x-His tag, the thrombin cleavage site, and the linker are all positioned within the construct between the deoxyribonucleic acid molecule and the SecM stalling sequence.

9. The method of claim 1, wherein said recovering is carried out by affinity selection with an agent specific for the protein.

10. The method of claim 1, wherein the protein is a single-chain variable fragment antibody.

11. The method of claim 1, wherein the cell is a bacterial cell.

12. The method of claim 11, wherein the bacterial cell is E. coli.

13. The method of claim 1, wherein the deoxyribonucleic acid molecule is coupled to the stall sequence by way of a linker sequence.

14. The method of claim 13, wherein the linker sequence is selected from the group consisting of (i) a Glycine-Serine linker comprising 10 to 50 Glycine/Serine units and (ii) a linker sequence having the amino acid sequence of SEQ ID NO:27.

15. The method of claim 2 further comprising: characterizing the enriched protein.

16. The method of claim 9, wherein the agent is the target molecule.

17. The method of claim 12, wherein the bacterial cell is an Origami strain of E. coli.

18. The method of claim 1, wherein the construct comprises two or more deoxyribonucleic acid molecules encoding two or more proteins which bind to the target molecule.

19. A method comprising:
providing a construct comprising a deoxyribonucleic acid molecule encoding a protein which binds to a target molecule, said deoxyribonucleic acid molecule being coupled to a stall sequence;
transforming a host cell with the construct; and
culturing the host cell under conditions effective to form a complex within the host cell, the complex comprising the protein whose translation has been stalled, an mRNA encoding the protein, and ribosomes, wherein the protein in the complex is in a properly folded, active form, wherein the protein is a ligand binding protein selected from the group consisting of high-affinity antibody fragments, single-chain Fv antibody fragments, nanobodies, nanobody fragments, fluorobodies, and aptamers.

20. The method of claim 19 further comprising:
recovering the complex from the cell;
isolating the mRNA from the recovered complex;
reverse transcribing the isolated mRNA to form a cDNA encoding the protein;
forming a construct comprising the cDNA coupled to the stall sequence; and
repeating said transforming, said culturing, and said recovering to enrich the protein recovered.

21. The method of claim 20, wherein said isolating comprises:
dissociating the complex.

22. The method of claim 20 further comprising: characterizing the enriched ligand binding protein.

23. The method of claim 20, wherein said isolating, said reverse transcribing, said forming, and said repeating are carried out multiple times.

24. The method of claim 19, wherein the stall sequence is SecM coupled to the deoxyribonucleic acid molecule.

25. The method of claim 19, wherein said recovering is carried out by affinity selection with the target molecule.

26. The method of claim 19, wherein the protein is a single-chain variable fragment antibody.

27. The method of claim 19, wherein the cell is a bacterial cell.

28. The method of claim 27, wherein the bacterial cell is *E. coli.*

29. The method of claim 28, wherein the bacterial cell is an Origami strain of *E. coli.*

30. The method of claim 19, wherein the deoxyribonucleic acid molecule is coupled to the stall sequence by way of a linker sequence.

31. The method of claim 30, wherein the linker sequence is selected from the group consisting of (i) a Glycine-Serine linker comprising 10 to 50 Glycine/Serine units and (ii) a linker sequence having the amino acid sequence of SEQ ID NO:27.

32. The method of claim 19, wherein the construct comprises two or more deoxyribonucleic acid molecules encoding two or more proteins which bind to the target molecule.

33. The method of claim 1, wherein the stall sequence has the amino acid sequence of FXXXXWIXXXXGIRAGP (SEQ ID NO: 26), wherein X is any amino acid.

34. The method of claim 19, wherein the stall sequence has the amino acid sequence of FXXXXWIXXXXGIRAGP (SEQ ID NO: 26), wherein X is any amino acid.

\* \* \* \* \*

SEQUENCE LISTING

```
<160> NUMBER OF SEQ ID NOS: 28

<210> SEQ ID NO 1
<211> LENGTH: 17
<212> TYPE: PRT
<213> ORGANISM: Escherichia coli

<400> SEQUENCE: 1

Phe Ser Thr Pro Val Trp Ile Ser Gln Ala Gln Gly Ile Arg Ala Gly
1               5                   10                  15

Pro

<210> SEQ ID NO 2
<211> LENGTH: 286
<212> TYPE: PRT
<213> ORGANISM: Artificial
<220> FEATURE:
<223> OTHER INFORMATION: primer

<400> SEQUENCE: 2

Met Ala Asp Tyr Lys Asp Asp Asp Lys Gly Gly Ser Ala Glu Val
1               5                   10                  15

Gln Leu Val Glu Ser Gly Gly Gly Leu Val Lys Pro Gly Gly Ser Leu
            20                  25                  30

Arg Leu Ser Cys Ala Ala Ser Gly Phe Thr Phe Ser Asn Tyr Ser Met
        35                  40                  45

Asn Trp Val Arg Gln Ala Pro Gly Lys Gly Leu Glu Trp Val Ser Ser
    50                  55                  60
```

```
Ile Ser Ser Ser Ser Ser Tyr Ile Tyr Tyr Ala Asp Phe Val Lys Gly
 65                  70                  75                  80

Arg Phe Thr Ile Ser Arg Asp Asn Ala Lys Asn Ser Leu Tyr Leu Gln
                 85                  90                  95

Met Asn Ser Leu Arg Ala Glu Asp Thr Ala Val Tyr Tyr Cys Ala Arg
            100                 105                 110

Ser Ser Ile Thr Ile Phe Gly Gly Gly Met Asp Val Trp Gly Arg Gly
        115                 120                 125

Thr Leu Val Thr Val Ser Ser Gly Gly Gly Gly Ser Gly Gly Gly Gly
    130                 135                 140

Ser Gly Gly Gly Gly Ser Gln Ser Val Leu Thr Gln Pro Ala Ser Val
145                 150                 155                 160

Ser Gly Ser Pro Gly Gln Ser Ile Thr Ile Ser Cys Ala Gly Thr Ser
                165                 170                 175

Ser Asp Val Gly Gly Tyr Asn Tyr Val Ser Trp Tyr Gln Gln His Pro
            180                 185                 190

Gly Lys Ala Pro Lys Leu Met Ile Tyr Glu Gly Ser Lys Arg Pro Ser
        195                 200                 205

Gly Val Ser Asn Arg Phe Ser Gly Ser Lys Ser Gly Asn Thr Ala Ser
    210                 215                 220

Leu Thr Ile Ser Gly Leu Gln Ala Glu Asp Glu Ala Asp Tyr Tyr Cys
225                 230                 235                 240

Ser Ser Tyr Thr Thr Arg Ser Thr Arg Val Phe Gly Gly Gly Thr Lys
                245                 250                 255

Leu Ala Val Leu Gly Ala Ala Ala Glu Gln Lys Leu Ile Ser Glu Glu
            260                 265                 270

Asp Leu Asn Gly Ala Ala Glu Leu His His His His His His
        275                 280                 285

<210> SEQ ID NO 3
<211> LENGTH: 286
<212> TYPE: PRT
<213> ORGANISM: Artificial
<220> FEATURE:
<223> OTHER INFORMATION: primer

<400> SEQUENCE: 3

Met Ala Asp Tyr Lys Asp Asp Asp Lys Gly Gly Ser Ala Glu Val
 1               5                  10                  15

Gln Leu Val Glu Ser Gly Gly Gly Leu Val Lys Pro Gly Gly Ser Leu
             20                  25                  30

Arg Leu Ser Cys Ala Ala Ser Gly Phe Thr Phe Ser Asn Asn Ser Met
         35                  40                  45

Asn Trp Val Arg Gln Ala Pro Gly Lys Gly Leu Glu Trp Val Ser Ser
     50                  55                  60

Ile Ser Ser Ser Ser Tyr Ile Tyr Tyr Ala Asp Phe Val Lys Gly
 65                  70                  75                  80

Arg Phe Thr Ile Ser Arg Asp Asn Ala Lys Asn Ser Leu Tyr Leu Gln
                 85                  90                  95

Met Asn Ser Leu Arg Ala Glu Asp Thr Ala Val Tyr Tyr Cys Ala Arg
            100                 105                 110

Ser Ser Thr Thr Ile Phe Gly Gly Gly Met Asp Val Trp Gly Arg Gly
        115                 120                 125

Thr Leu Val Thr Val Ser Ser Gly Gly Gly Gly Ser Gly Glu Gly Gly
    130                 135                 140
```

```
Ser Gly Gly Gly Gly Ser Gln Ser Val Leu Thr Gln Pro Ala Ser Val
145                 150                 155                 160

Ser Gly Ser Pro Gly Gln Ser Ile Thr Ile Ser Cys Ala Gly Thr Ser
                165                 170                 175

Ser Asp Val Gly Gly Tyr Asn Tyr Val Ser Trp Tyr Gln Gln His Pro
            180                 185                 190

Gly Lys Ala Pro Lys Leu Met Ile Tyr Glu Asp Ser Lys Arg Pro Ser
        195                 200                 205

Gly Val Ser Asn Arg Phe Ser Gly Ser Lys Ser Gly Asn Thr Ala Ser
    210                 215                 220

Leu Thr Ile Ser Gly Leu Gln Ala Glu Asp Glu Ala Asp Tyr Tyr Cys
225                 230                 235                 240

Ser Ser Tyr Thr Thr Arg Ser Thr Arg Val Phe Gly Gly Gly Thr Lys
                245                 250                 255

Leu Ala Val Leu Gly Ala Ala Ala Glu Gln Lys Leu Ile Ser Glu Gly
            260                 265                 270

Asp Leu Asn Gly Ala Ala Glu Leu His His His His His His
        275                 280                 285
```

```
<210> SEQ ID NO 4
<211> LENGTH: 286
<212> TYPE: PRT
<213> ORGANISM: Artificial
<220> FEATURE:
<223> OTHER INFORMATION: primer

<400> SEQUENCE: 4
```

```
Met Ala Asp Tyr Lys Asp Asp Asp Lys Gly Gly Ser Ala Glu Val
1               5                   10                  15

Gln Leu Val Glu Ser Gly Gly Gly Leu Val Lys Pro Gly Gly Ser Leu
            20                  25                  30

Arg Leu Ser Cys Ala Ala Ser Gly Phe Thr Phe Ser Asn Tyr Ser Met
        35                  40                  45

Asn Trp Val Arg Gln Ala Pro Gly Lys Gly Leu Glu Trp Ile Ser Ser
    50                  55                  60

Ile Ser Ser Ser Ser Tyr Ile Tyr Tyr Ala Asp Phe Val Lys Gly
65                  70                  75                  80

Arg Phe Thr Ile Ser Arg Asp Asn Val Lys Asn Ser Leu Tyr Leu Gln
                85                  90                  95

Met Asn Ser Leu Arg Ala Glu Asp Thr Ala Val Tyr Tyr Cys Ala Arg
            100                 105                 110

Ser Ser Ile Thr Ile Phe Gly Gly Met Asp Val Trp Gly Arg Gly
        115                 120                 125

Thr Leu Val Thr Val Ser Ser Gly Gly Gly Ser Gly Gly Gly Gly
    130                 135                 140

Ser Gly Gly Gly Gly Ser Gln Ser Val Leu Thr Gln Pro Ala Ser Val
145                 150                 155                 160

Ser Gly Ser Pro Gly Gln Ser Ile Thr Ile Ser Cys Ala Gly Thr Ser
                165                 170                 175

Ser Asp Val Gly Gly Tyr Asn Tyr Val Ser Trp Tyr Gln Gln His Leu
            180                 185                 190

Gly Lys Ala Pro Lys Leu Met Ile Tyr Glu Gly Ser Lys Arg Ser Ser
        195                 200                 205

Gly Val Ser Asn Arg Phe Ser Gly Ser Lys Ser Gly Asn Thr Ala Ser
    210                 215                 220
```

```
Leu Thr Ile Ser Gly Leu Gln Ala Glu Asp Glu Ala Asp Tyr Tyr Cys
225                 230                 235                 240

Ser Ser Tyr Thr Thr Arg Ser Thr Arg Val Phe Gly Gly Gly Thr Lys
            245                 250                 255

Leu Ala Val Leu Gly Ala Ala Ala Glu Gln Lys Leu Ile Ser Glu Glu
        260                 265                 270

Asp Leu Asn Gly Ala Ala Glu Leu His His His His His His
        275                 280                 285
```

<210> SEQ ID NO 5
<211> LENGTH: 30
<212> TYPE: DNA
<213> ORGANISM: Artificial
<220> FEATURE:
<223> OTHER INFORMATION: primer

<400> SEQUENCE: 5
ctcatggtcg acttcagcac gcccgtctgg                                30

<210> SEQ ID NO 6
<211> LENGTH: 41
<212> TYPE: DNA
<213> ORGANISM: Artificial
<220> FEATURE:
<223> OTHER INFORMATION: primer

<400> SEQUENCE: 6
ctcatgctcg agttaaagct tctgcgcaac tgttgggaag c                    41

<210> SEQ ID NO 7
<211> LENGTH: 42
<212> TYPE: DNA
<213> ORGANISM: Artificial
<220> FEATURE:
<223> OTHER INFORMATION: primer

<400> SEQUENCE: 7
ggcatccgtg ctggccctaa gcttcaacgc ctcacctaac aa                   42

<210> SEQ ID NO 8
<211> LENGTH: 43
<212> TYPE: DNA
<213> ORGANISM: Artificial
<220> FEATURE:
<223> OTHER INFORMATION: primer

<400> SEQUENCE: 8
gttgttaggt gaggcgttga agcttagggc cagcacggat gcc                  43

<210> SEQ ID NO 9
<211> LENGTH: 56
<212> TYPE: DNA
<213> ORGANISM: Artificial
<220> FEATURE:
<223> OTHER INFORMATION: primer

<400> SEQUENCE: 9
gcgatgccat ggccgactac aaggacgatg acgacaaggg agccgaggtg cagctg    56

<210> SEQ ID NO 10
<211> LENGTH: 26
<212> TYPE: DNA
<213> ORGANISM: Artificial
<220> FEATURE:
<223> OTHER INFORMATION: primer

```
<400> SEQUENCE: 10
gcgatggtcg actgcggccc attcag                                            26

<210> SEQ ID NO 11
<211> LENGTH: 42
<212> TYPE: DNA
<213> ORGANISM: Artificial
<220> FEATURE:
<223> OTHER INFORMATION: primer

<400> SEQUENCE: 11
ggatctgaat ggggccgcag agctcgtcga cttcagcacg cc                          42

<210> SEQ ID NO 12
<211> LENGTH: 42
<212> TYPE: DNA
<213> ORGANISM: Artificial
<220> FEATURE:
<223> OTHER INFORMATION: primer

<400> SEQUENCE: 12
ggcgtgctga agtcgacgag ctctgcggcc ccattcagat cc                          42

<210> SEQ ID NO 13
<211> LENGTH: 8
<212> TYPE: PRT
<213> ORGANISM: Artificial
<220> FEATURE:
<223> OTHER INFORMATION: linker sequence

<400> SEQUENCE: 13

Ala Gly Ser Ala Ala Gly Ser Gly
1               5

<210> SEQ ID NO 14
<211> LENGTH: 46
<212> TYPE: DNA
<213> ORGANISM: Artificial
<220> FEATURE:
<223> OTHER INFORMATION: primer

<400> SEQUENCE: 14
ctcatggagc tccatcatca tcatcatcac agcagcggcc tggtgc                      46

<210> SEQ ID NO 15
<211> LENGTH: 29
<212> TYPE: DNA
<213> ORGANISM: Artificial
<220> FEATURE:
<223> OTHER INFORMATION: primer

<400> SEQUENCE: 15
ctcatggtcg acgccagaac cagcagcgg                                         29

<210> SEQ ID NO 16
<211> LENGTH: 44
<212> TYPE: DNA
<213> ORGANISM: Artificial
```

```
<220> FEATURE:
<223> OTHER INFORMATION: primer

<400> SEQUENCE: 16
gtgccgcgcg gcagccatga attcatgcat gctataaata ttgc         44

<210> SEQ ID NO 17
<211> LENGTH: 44
<212> TYPE: DNA
<213> ORGANISM: Artificial
<220> FEATURE:
<223> OTHER INFORMATION: primer

<400> SEQUENCE: 17
gcaatattta tagcatgcat gaattcatgg ctgccgcgcg gcac         44

<210> SEQ ID NO 18
<211> LENGTH: 37
<212> TYPE: DNA
<213> ORGANISM: Artificial
<220> FEATURE:
<223> OTHER INFORMATION: primer

<400> SEQUENCE: 18
gaggaggttt tagaggaatt cggatccgct ggctccg              37

<210> SEQ ID NO 19
<211> LENGTH: 37
<212> TYPE: DNA
<213> ORGANISM: Artificial
<220> FEATURE:
<223> OTHER INFORMATION: primer

<400> SEQUENCE: 19
cggagccagc ggatccgaat tcctctaaaa cctcctc              37

<210> SEQ ID NO 20
<211> LENGTH: 56
<212> TYPE: DNA
<213> ORGANISM: Artificial
<220> FEATURE:
<223> OTHER INFORMATION: primer

<400> SEQUENCE: 20
gcgatgccat ggccgactac aaggacgatg acgacaaggg agccgaggtg cagctg    56

<210> SEQ ID NO 21
<211> LENGTH: 30
<212> TYPE: DNA
<213> ORGANISM: Artificial
<220> FEATURE:
<223> OTHER INFORMATION: primer

<400> SEQUENCE: 21
gcgatggagc tcttatgcgg ccccattcag                     30

<210> SEQ ID NO 22
<211> LENGTH: 56
<212> TYPE: DNA
<213> ORGANISM: Artificial
<220> FEATURE:
<223> OTHER INFORMATION: primer
```

<400> SEQUENCE: 22
gcgatgccat ggccgactac aaggacgatg acgacaaggg agccgaggtg cagctg            56

<210> SEQ ID NO 23
<211> LENGTH: 27
<212> TYPE: DNA
<213> ORGANISM: Artificial
<220> FEATURE:
<223> OTHER INFORMATION: primer

<400> SEQUENCE: 23
gcgatggtcg actgcggccc cattcag                                            27

<210> SEQ ID NO 24
<211> LENGTH: 30
<212> TYPE: DNA
<213> ORGANISM: Artificial
<220> FEATURE:
<223> OTHER INFORMATION: primer

<400> SEQUENCE: 24
gcgatggagc tcttatgcgg ccccattcag                                         30

<210> SEQ ID NO 25
<211> LENGTH: 65
<212> TYPE: DNA
<213> ORGANISM: Artificial
<220> FEATURE:
<223> OTHER INFORMATION: Primer

<400> SEQUENCE: 25
gcggcgatgc catggccgac tacaaggacg atgacgacaa gggaggatcc gccgaggtgc        60
agctg                                                                    65

<210> SEQ ID NO 26
<211> LENGTH: 17
<212> TYPE: PRT
<213> ORGANISM: Artificial
<220> FEATURE:
<223> OTHER INFORMATION: SecM consensus sequence
<220> FEATURE:
<221> NAME/KEY: misc_feature
<222> LOCATION: (2)..(5)
<223> OTHER INFORMATION: Xaa can be any naturally occurring amino acid
<220> FEATURE:
<221> NAME/KEY: misc_feature
<222> LOCATION: (8)..(11)
<223> OTHER INFORMATION: Xaa can be any naturally occurring amino acid

<400> SEQUENCE: 26

Phe Xaa Xaa Xaa Xaa Trp Ile Xaa Xaa Xaa Xaa Gly Ile Arg Ala Gly
1               5                   10                  15

Pro

<210> SEQ ID NO 27
<211> LENGTH: 8
<212> TYPE: PRT
<213> ORGANISM: Artificial
<220> FEATURE:
<223> OTHER INFORMATION: linker sequence

<400> SEQUENCE: 27

Ala Gly Ser Ala Ala Gly Ser Gly
1               5

```
<210> SEQ ID NO 28
<211> LENGTH: 51
<212> TYPE: DNA
<213> ORGANISM: Escherichia coli

<400> SEQUENCE: 28
ttcagcacgc ccgtctggat aagccaggcg caaggcatcc gtgctggccc t          51
```